(12) United States Patent
Taylor et al.

(10) Patent No.: US 11,969,179 B2
(45) Date of Patent: Apr. 30, 2024

(54) SINGLE INCISION LAPAROSCOPIC TISSUE RETRIEVAL SYSTEM

(71) Applicant: Applied Medical Resources Corporation, Rancho Santa Margarita, CA (US)

(72) Inventors: Scott V. Taylor, Rancho Santa Margarita, CA (US); Henry Kahle, Corona, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 155 days.

(21) Appl. No.: 17/519,380

(22) Filed: Nov. 4, 2021

(65) Prior Publication Data

US 2022/0054154 A1 Feb. 24, 2022

Related U.S. Application Data

(63) Continuation of application No. 16/275,911, filed on Feb. 14, 2019, now Pat. No. 11,191,557, which is a
(Continued)

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00287* (2013.01)

(58) Field of Classification Search
CPC ............ A61B 17/221; A61B 17/00234; A61B 2017/2212; A61B 2017/00287; A61B 1/00085
See application file for complete search history.

(56) References Cited

U.S. PATENT DOCUMENTS 30,471 A 10/1860 Dudley
1,609,014 A 11/1926 Dowd
(Continued)

FOREIGN PATENT DOCUMENTS

DE 25796 1/1884
DE 4216165 11/1992
(Continued)

OTHER PUBLICATIONS

The International Bureau of WIPO, The International Preliminary Report on Patentability for International Application No. PCT/US2006/060007 dated Apr. 24, 2008.
(Continued)

*Primary Examiner* — Diane D Yabut
(74) *Attorney, Agent, or Firm* — John F. Heal

(57) ABSTRACT

A tissue retrieval system can include a tissue retrieval bag with an elongate profile. The tissue retrieval bag can have a relatively large volume, but be rollable to a stowed configuration to fit in a relatively small diameter introducer. The tissue retrieval system can include one or more support arms coupled to the tissue retrieval bag, the support arms biased to position the tissue retrieval bag in an access position once deployed from the introducer. A tissue retrieval system can have a hybrid tissue retrieval bag including material properties that vary along the depth of the bag from an open end to a closed end. A tissue retrieval bag can be used in conjunction with an introducer, or as a stand alone tissue retrieval bag.

12 Claims, 13 Drawing Sheets

Related U.S. Application Data continuation of application No. 14/715,086, filed on May 18, 2015, now Pat. No. 10,245,053, which is a continuation of application No. 12/902,055, filed on Oct. 11, 2010, now Pat. No. 9,033,995.

(60) Provisional application No. 61/389,101, filed on Oct. 1, 2010, provisional application No. 61/250,364, filed on Oct. 9, 2009.

(56) References Cited

U.S. PATENT DOCUMENTS

| | | |
|---|---|---|
| 3,476,114 A | 11/1969 | Shannon et al. |
| 3,476,115 A | 11/1969 | Graeff et al. |
| 4,287,807 A | 9/1981 | Pacharis et al. |
| 4,428,375 A | 1/1984 | Ellman |
| 4,732,150 A | 3/1988 | Keener Jr. |
| 4,741,335 A | 5/1988 | Okada |
| 4,991,593 A | 2/1991 | Levahn |
| 5,037,379 A | 8/1991 | Clayman et al. |
| 5,074,867 A | 12/1991 | Wilk |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,195,507 A | 3/1993 | Bilweis |
| 5,201,740 A | 4/1993 | Nakao et al. |
| 5,215,521 A | 6/1993 | Cochran et al. |
| 5,224,930 A * | 7/1993 | Spaeth .............. A61B 17/34 606/128 |
| 5,234,439 A | 8/1993 | Wilk et al. |
| 5,279,539 A | 1/1994 | Bohan et al. |
| 5,279,548 A | 1/1994 | Essig et al. |
| 5,308,327 A | 5/1994 | Heaven et al. |
| 5,312,416 A | 5/1994 | Spaeth et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,366,460 A | 11/1994 | Eberbach |
| 5,368,597 A | 11/1994 | Pagedas |
| 5,417,684 A | 5/1995 | Jackson et al. |
| 5,417,697 A | 5/1995 | Wilk et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| RE35,164 E | 3/1996 | Kindberg et al. |
| 5,509,923 A | 4/1996 | Middleman et al. |
| 5,524,633 A | 6/1996 | Heaven et al. |
| 5,535,759 A | 7/1996 | Wilk |
| 5,601,572 A | 2/1997 | Middleman et al. |
| 5,611,803 A | 3/1997 | Heaven et al. |
| 5,613,973 A | 3/1997 | Jackson et al. |
| 5,632,746 A | 5/1997 | Middleman et al. |
| 5,643,283 A | 7/1997 | Younker |
| 5,647,372 A | 7/1997 | Tovey et al. |
| 5,655,657 A | 8/1997 | Roshdy |
| 5,656,012 A | 8/1997 | Sienkiewicz |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,749,879 A | 5/1998 | Middleman et al. |
| 5,755,724 A | 5/1998 | Yoon |
| 5,759,187 A | 6/1998 | Nakao et al. |
| 5,779,716 A | 7/1998 | Cano et al. |
| 5,782,839 A | 7/1998 | Hart et al. |
| 5,785,677 A | 7/1998 | Auweiler |
| 5,788,709 A | 8/1998 | Riek et al. |
| 5,809,621 A | 9/1998 | McCree et al. |
| 5,820,628 A | 10/1998 | Middleman et al. |
| 5,836,953 A | 11/1998 | Yoon |
| 5,853,374 A | 12/1998 | Hart et al. |
| 5,904,690 A | 5/1999 | Middleman et al. |
| 5,947,978 A | 9/1999 | Holsinger |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,015,415 A | 1/2000 | Avellanet |
| 6,019,770 A | 2/2000 | Christoudias |
| 6,059,793 A | 5/2000 | Pagedas |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,350,267 B1 | 2/2002 | Stefanchik |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,575,988 B2 | 6/2003 | Rousseau |
| 6,805,699 B2 | 10/2004 | Shimm |
| 6,814,739 B2 | 11/2004 | Secrest et al. |
| 6,958,069 B2 | 10/2005 | Shipp et al. |
| 6,986,774 B2 | 1/2006 | Middleman et al. |
| 7,041,055 B2 | 5/2006 | Young et al. |
| 7,115,125 B2 | 10/2006 | Nakao |
| 7,270,663 B2 | 9/2007 | Nakao |
| 7,547,310 B2 | 6/2009 | Whitfield |
| 7,618,437 B2 | 11/2009 | Nakao |
| 7,670,346 B2 | 3/2010 | Whitfield |
| 8,062,306 B2 | 11/2011 | Nobis et al. |
| 2003/0100919 A1 | 5/2003 | Hopkins et al. |
| 2004/0087969 A1 | 5/2004 | Kayan |
| 2004/0097960 A1 | 5/2004 | Terachi et al. |
| 2004/0138587 A1 | 7/2004 | Lyons |
| 2004/0158261 A1 | 8/2004 | Vu |
| 2004/0193184 A1 | 9/2004 | Laufer et al. |
| 2004/0254573 A1 | 12/2004 | Dycus |
| 2005/0165411 A1 | 7/2005 | Orban |
| 2005/0267489 A1 | 12/2005 | Secrest et al. |
| 2005/0267492 A1 | 12/2005 | Poncet et al. |
| 2006/0052799 A1 | 3/2006 | Middleman et al. |
| 2006/0229639 A1 | 3/2006 | Whitfield |
| 2006/0074406 A1 | 4/2006 | Cooper et al. |
| 2006/0200169 A1 | 9/2006 | Sniffin |
| 2006/0200170 A1 | 9/2006 | Aranyi |
| 2006/0276805 A1 | 12/2006 | Yu |
| 2007/0088370 A1 | 4/2007 | Kahle et al. |
| 2008/0033451 A1 | 2/2008 | Rieber et al. |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2009/0043315 A1 | 2/2009 | Moon |
| 2009/0082779 A1 | 3/2009 | Nakao |
| 2009/0192510 A1 | 7/2009 | Bahney |
| 2009/0306683 A1 | 12/2009 | Zwolinski et al. |
| 2010/0076451 A1 | 3/2010 | Zwolinski et al. |
| 2010/0152609 A1 | 6/2010 | Zwolinski et al. |
| 2010/0152746 A1 | 6/2010 | Ceniccola et al. |

FOREIGN PATENT DOCUMENTS

| | | |
|---|---|---|
| DE | 197 07 361 | 8/1998 |
| EP | 499243 | 8/1992 |
| EP | 0 947 166 | 10/1999 |
| EP | 1 679 040 A1 | 7/2006 |
| EP | 1 707 126 A1 | 10/2006 |
| EP | 2 617 365 A2 | 7/2013 |
| JP | 6-154161 | 6/1994 |
| SU | 1537229 | 1/1990 |
| SU | 5-115493 | 5/1993 |
| WO | WO 1993/15671 | 8/1993 |
| WO | WO 1993/24063 | 12/1993 |

(56) References Cited

FOREIGN PATENT DOCUMENTS

| WO | WO 1994/13215 | 6/1994 |
|----|----|----|
| WO | WO 96/16601 A1 | 6/1996 |
| WO | WO 2003/105674 | 12/2003 |
| WO | WO 2007/081601 | 7/2007 |
| WO | WO 2008/114234 A2 | 9/2008 |
| WO | WO 2020/102714 A2 | 5/2020 |

OTHER PUBLICATIONS

The International Bureau of WIPO, The International Preliminary Report for Patentability for International Application No. PCT/US2010/052190 dated Apr. 11, 2012 entitled "Single Incision Laparoscopic Tissue Retrieval System".

International Searching Authority, The International Search Report and Written Opinion for International Application No. PCT/US2011/054647,entitled Laparoscopic Tissue Retrieval System, dated Feb. 21, 2012,.

The International Bureau of WIPO, The International Preliminary Report on Patentability for International Application No. PCT/US2006/060022, dated Jul. 24, 2008.

European Patent Office, International Search Report and Written Opinion of theInternational Searching Authority for International Application No. PCT/US2006/060007 dated Mar. 2, 2007.

European Patent Office, International Search Report and Written Opinion of the International Searching Authority for International Application No. PCT/US2006/060022 dated Jun. 5, 2007.

International Search Report and Written Opinion for International Application No. PCT/US2010/052190, dated Feb. 3, 2011, titled Single Incision Laparoscopic Tissue Retrieval System.

United States Surgical, Tyco Healthcare Group LP, Autosuture* Endocatch* Gold 10 mm Single-Use Specimen Pouch, 10000-25912, Product Information Data Sheet, Feb. 2004, 2 pages.

United States Surgical, Tyco Healthcare Group LP, Autosuture* Endocatch* II|Single-Use Specimen Pouch, 10000-19724, Product Information Data Sheet, Aug. 2002, 2 pages.

Conmed Corporation, EndoSurgery Products, Hand Held Laparoscopic Instruments, Product Descriptions (Web pages), 2004, 3 pages.

Cook Group Inc., Cook Urological, Cook® Drainage Pouch Sets, Product Description (Web page), 2003, 1 page.

Johnson & Johnson Gateway LLC, Ethicon Endo-Surgery Inc., Endoscopic Product Family, Endopouch Retriever Specimen Retrieval Bag, Product Description (Web Page), 2000-2005, 1 page.

Co-Pending U.S. Appl. No. 11/549,701, filed Oct. 16, 2006, Title: Device for Isolating and Removing Tissue From a Body Cavity, and its associated file history.

Co-Pending U.S. Appl. No. 11/549,971, filed Oct. 16, 2006; Title: Tissue Retrieval System, and its associated file history.

U.S. Pat. No. 5,853,374, filed Oct. 11, 1995 entitled Tissue Retrieval System and associated file history (now abandoned).

U.S. Appl. No. 12/902,055, filed Oct. 11, 2010 entitled "Single Incision Laparoscopic Tissue Retrieval System" and associated file history.

U.S. Appl. No. 13/252,110, filed Oct. 3, 2011, entitled "Laparoscopic Tissue Retrieval System" and associated file history.

European Patent Office, Extended European Search Report for European Patent Application No. EP 19177060.1, titled "Single Incision Laparoscopic Tissue Retrieval System", dated Sep. 16, 2019, 10 pgs.

International Searching Authority, International Search Report and Written Opinion for International Application No. PCT/US2020/060592, entitled "Redeployable Tissue Retrieval System," datled Apr. 13, 2021, 17 pgs.

* cited by examiner

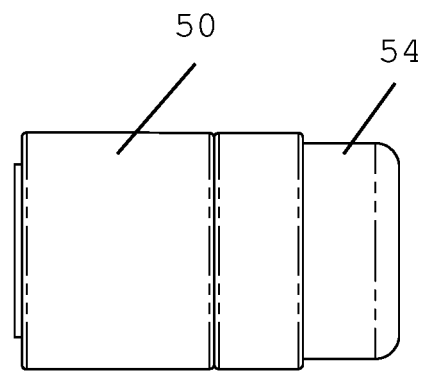
FIG. 4B
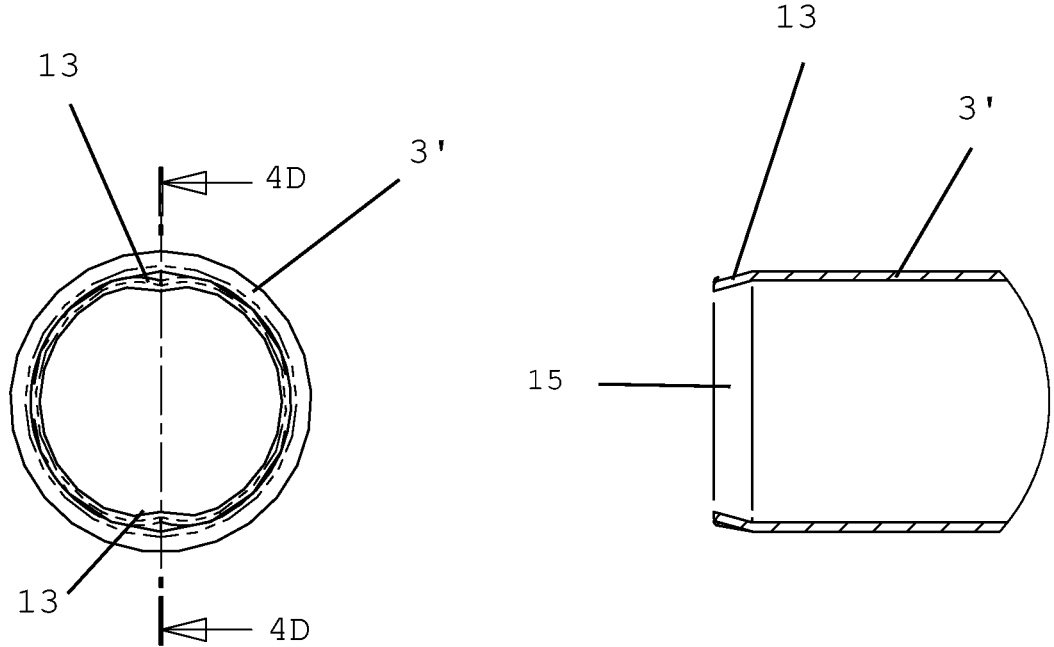
FIG. 4C  FIG. 4D

SINGLE INCISION LAPAROSCOPIC TISSUE RETRIEVAL SYSTEM

CROSS REFERENCE TO RELATED APPLICATIONS

This application is a continuation of U.S. patent application Ser. No. 16/275,911 entitled "SINGLE INCISION LAPAROSCOPIC TISSUE RETRIEVAL SYSTEM," filed Feb. 14, 2019, currently pending, which is a continuation of U.S. patent application Ser. No. 14/715,086 entitled "SINGLE INCISION LAPAROSCOPIC TISSUE RETRIEVAL SYSTEM," filed May 18, 2015, which issued as U.S. Pat. No. 10,245,053, which is a continuation of U.S. patent application Ser. No. 12/902,055 entitled "SINGLE INCISION LAPAROSCOPIC TISSUE RETRIEVAL SYSTEM," filed Oct. 11, 2010, which issued as U.S. Pat. No. 9,033,995, and which claims the benefit of U.S. Provisional Patent Application No. 61/389,101 entitled "TISSUE RETRIEVAL SYSTEM WITH HYBRID RETRIEVAL BAG," filed Oct. 1, 2010, and U.S. Provisional Patent Application No. 61/250,364, entitled "SINGLE INCISION LAPAROSCOPIC TISSUE RETRIEVAL SYSTEM," filed Oct. 9, 2009. The above-referenced applications are incorporated by reference herein in their entireties.

BACKGROUND OF THE INVENTION

Field of the Invention

The present application relates generally to apparatuses and methods for capturing and retrieving tissue from body cavities and in particular to a specimen retrieval bag device.

Description of the Related Art

Laparoscopic surgery is typically performed through trocars, which provide access across the abdominal wall and into the abdominal cavity. In some of surgeries, tissue disposed within the abdominal cavity is cut and removed from the body. However, removal of such tissue from the body may prove difficult due to the limited confines inherent with laparoscopic surgery and the available laparoscopic surgical instruments. For example, to reduce the invasiveness to a patient, it can be desirable to introduce all of the surgical instruments through a single laparoscopic port having a relatively small size. Also, removed tissue may include an infected or cancerous mass or organ, as well as blood, bile and other liquids, all referred to herein as tissue, which may pose infection issues or other complications if left within the body.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity.

SUMMARY OF THE INVENTION

In certain embodiments, a tissue retrieval system is provided herein. The tissue retrieval system comprises an elongate introducer, a tissue retrieval bag, and an actuator. The elongate introducer has a hollow lumen formed therein. The tissue retrieval bag has a proximal end, a distal end, and an opening. The tissue retrieval bag has an elongate profile such that the opening is positioned adjacent the proximal end and the tissue retrieval bag comprises a distal portion extending from the opening towards the distal end of the tissue retrieval bag. The actuator extends at least partially into the hollow lumen of the introducer. The tissue retrieval bag is actuatable by the actuator from a stowed position in which the tissue retrieval bag is positioned within the hollow lumen of the introducer to an open position in which the tissue retrieval bag is substantially outside the introducer.

In certain embodiments, a tissue retrieval system is provided herein. The tissue retrieval system comprises an introducer, a tissue retrieval bag, and an actuator. The introducer is sized and configured to be received in a trocar, the trocar having a diameter of less than about 7 mm. The introducer has a hollow lumen formed therein. The tissue retrieval bag has a volume of greater than approximately 100 mL. The tissue retrieval bag has a stowed configuration in which it is positionable within the hollow lumen of the introducer and an open configuration. The actuator is operable to advance the tissue retrieval bag from the stowed configuration within the introducer to the open configuration.

In certain embodiments, a tissue retrieval system is provided herein. The tissue retrieval system comprises an elongate tubular member, a tissue retrieval bag, and a support arm. The elongate tubular member has a passage formed therein. The elongate tubular member has a central longitudinal axis. The tissue retrieval bag has a stowed configuration in which the tissue retrieval bag is positionable within the passage of the elongate tubular member and an open configuration. The support arm is coupled to the tissue retrieval bag. The support arm is biased in a first direction radially outward from the central longitudinal axis and a second direction transverse to the central longitudinal axis to position the tissue retrieval bag in the open configuration in an access position.

In certain embodiments, a tissue retrieval bag is provided herein. The tissue retrieval bag comprises a film material. The film material has a proximal end, a distal end, and a rim defining an opening. The opening has a longitudinal axis. The opening is positioned adjacent the proximal end. The tissue retrieval bag comprises an elongate profile defined by a distal portion of the tissue retrieval bag extending distally of the opening with respect to the longitudinal axis.

In certain embodiments, a tissue retrieval device comprises a retrieval bag. The retrieval bag has an open end and a closed end. The retrieval bag has a first portion adjacent the open end, a second portion adjacent the closed end, and a joint coupling the first portion to the second portion. The first portion of the retrieval bag has a first compliance and the second portion of the retrieval bag has a second compliance, the first compliance being greater than the second compliance.

In certain embodiments, a tissue retrieval device comprises a thin film bag. The thin film bag has an open end and a closed end. The thin film bag comprises a first portion adjacent the open end and a second portion adjacent the closed end. The first portion and the second portion are formed of a film material. The first portion of the thin film bag has a first thickness and the second portion of the thin film bag has a second thickness, the first thickness is less than the second thickness.

In certain embodiments, a tissue retrieval device comprises a tissue bag having an open end, a closed end and an interior. The tissue bag comprises a first portion adjacent the open end, and a second portion adjacent the closed end. The second portion comprises a first layer, a second layer, a space between the first and second layer, and at least one vent fluidly coupling the space to ambient conditions exterior to the tissue bag.

In certain embodiments, a tissue retrieval device comprises a tissue bag having an open end and a closed end. The tissue bag comprises a cuff portion adjacent the open end, a first body portion between the cuff portion and a second body portion, and the second body portion adjacent the closed end. The cuff portion has a first compliance. The first body portion of the tissue bag has a second compliance. The second body portion of the tissue bag has a third compliance. The first compliance is greater than the second compliance, and the second compliance is greater than the third compliance.

BRIEF DESCRIPTION OF THE DRAWINGS

FIG. 4B is a side view of an embodiment of guide bead for the tissue retrieval bag of the tissue retrieval system of FIG. 1;

FIG. 4C is a front view of an embodiment of introducer tube of the tissue retrieval system of FIG. 1;

FIG. 4D is a partial cut away view of the introducer tube of FIG. 4C;

DETAILED DESCRIPTION OF THE INVENTION

Figure 1:
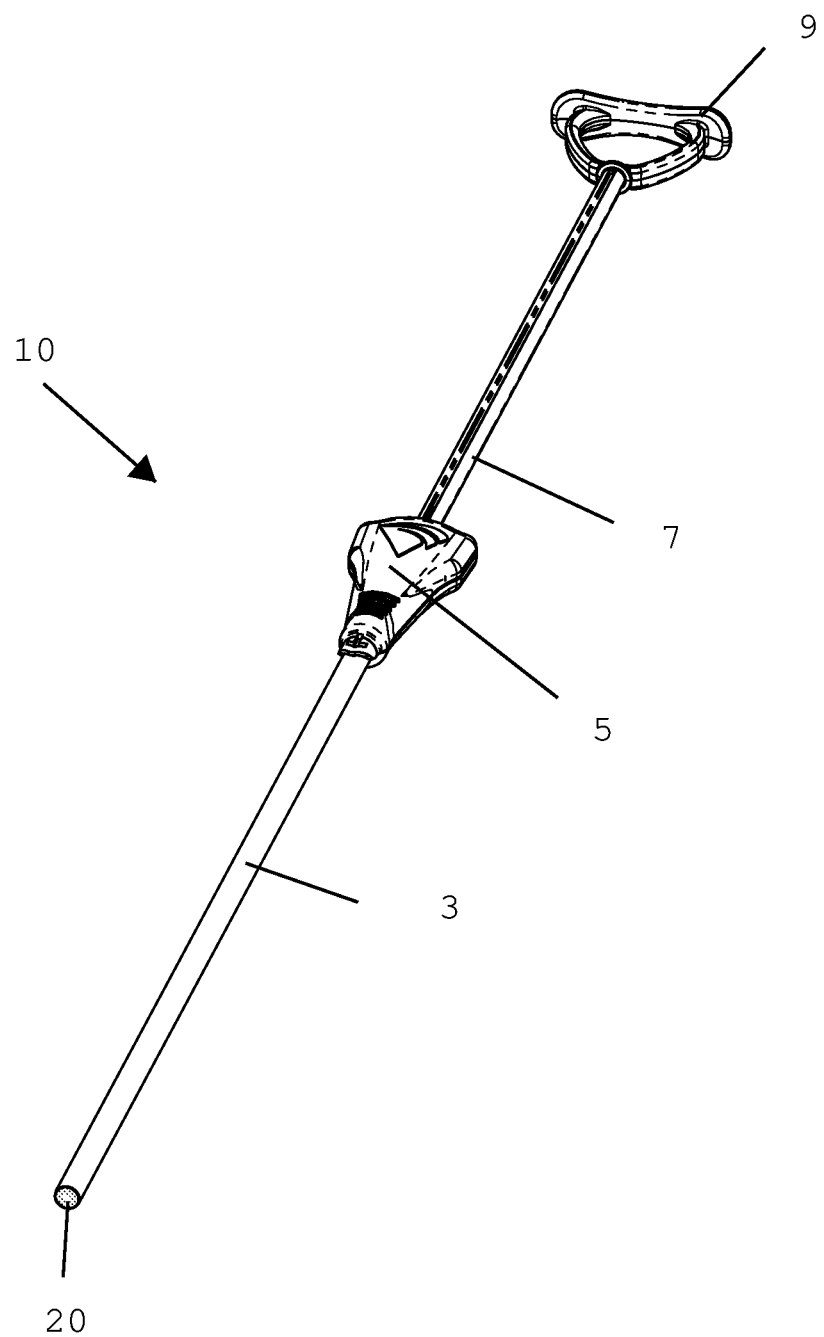
FIG. 1 is an isometric view of an embodiment of tissue retrieval system.

With reference to FIG. 1, an embodiment of tissue retrieval system 10 is illustrated. The illustrated tissue retrieval system can be used for containing and withdrawing excised tissue specimens from within a body cavity. For example, in some embodiments, the tissue retrieval system can be used to remove a patient's gallbladder from the patient's abdominal cavity. Thus, advantageously, the tissue retrieval systems discussed herein provide an easy to use tissue retrieval system which effectively contains excised tissue specimens to prevent loss or spillage of tissue specimens into a body cavity, and to protect the body wall access port site from contamination with the excised tissue specimens during withdrawal of the tissue specimens from within the body cavity.

With continued reference to FIG. 1, the tissue retrieval system 10 is illustrated in a non-deployed or non-activated initial condition. In the illustrated embodiment, the tissue retrieval system has an introducer 3 and an actuator or actuation rod 7. The introducer 3 in one aspect has a tubular configuration with a hollow lumen and a handle assembly 5 extending from a proximal end of the introducer 3. In some embodiments, the introducer 3 can be sized and configured for placement through a standard-size trocar. For example, it can be desirable that the introducer 3 can be sized as a 5 mm laparoscopic surgical instrument to be introduced through relatively small diameter trocars such as 5-7 mm trocars. In other embodiments, the introducer 3 can be sized as a 10 mm laparoscopic surgical instrument. In some embodiments, the introducer 3 can have a non-standard size for application at a specific location. In some embodiments, the tissue retrieval system 10 can include a relatively long introducer, such as, for example, a 45 cm long introducer 3 to improve access to the surgical site.

The handle assembly 5 of the illustrated embodiment can comprise a compact handle member that can be adapted for placement adjacent other surgical instruments in a single port laparoscopic surgical site. Thus, in some embodiments, the tissue retrieval system is adapted to be utilized during single incision laparoscopic procedures. In other embodiments, the handle assembly can include a pair of finger loops or grips formed with or otherwise coupled to the handle assembly 5 that can be utilized to hold or stabilize the introducer 3 as desired.

In the illustrated embodiment of tissue retrieval system 10, the introducer 3 has a proximal end and a distal end that are generally open, which can facilitate access to the hollow lumen. As illustrated, the actuator rod 7 extends into the hollow lumen from the open proximal end thereof, and at least a portion of the actuator rod 7 is slidably movable within the hollow lumen of the introducer 3. As further discussed with reference to FIGS. 2 and 3, with the tissue retrieval system 10 in the initial configuration, a tissue retrieval bag 20 in a stowed configuration can be positioned in the hollow lumen of the introducer 3. The actuator rod 7 in one aspect has a handle 9 extending from a proximal end thereof. The handle 9 provides a graspable portion of the device to control or facilitate movement of the actuator rod 7 relative to the introducer 3 between the initial condition of the tissue retrieval system 10 (illustrated in FIG. 1), and a deployed condition of the tissue retrieval system (illustrated in FIGS. 2-3).

Figure 2:
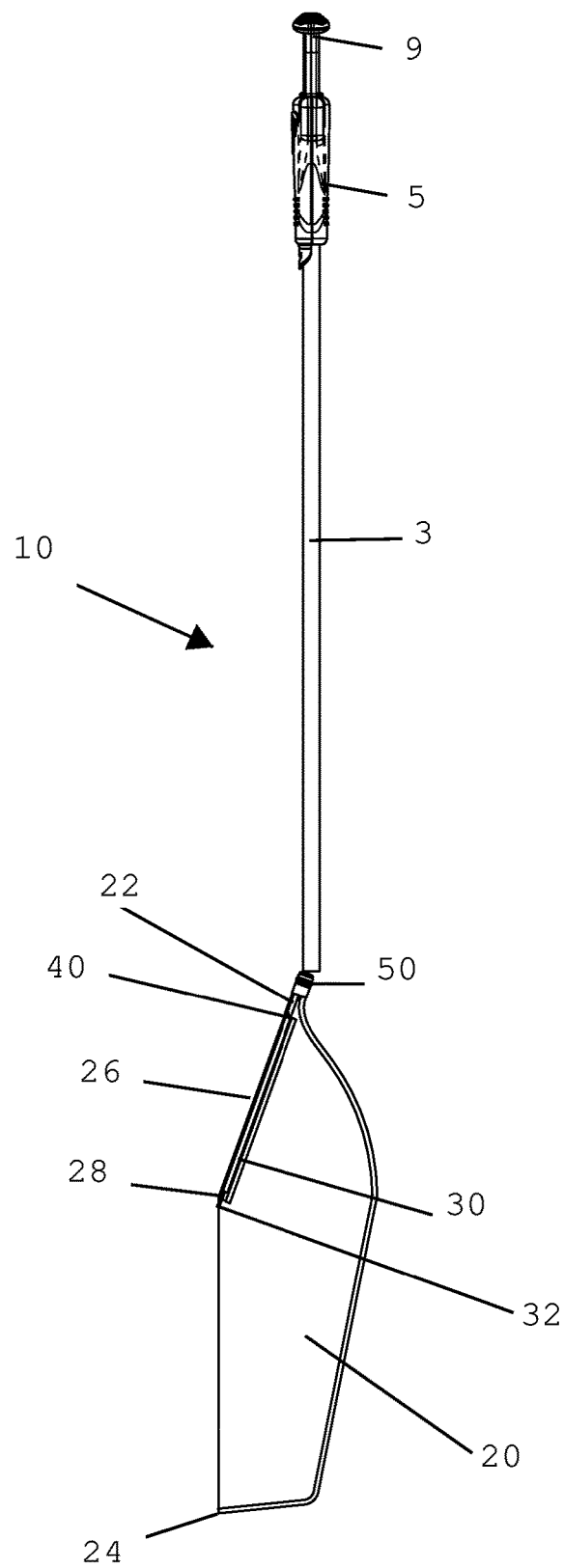
FIG. 2 is a side view of the tissue retrieval system of FIG. 1 with the retrieval bag deployed.
Figure 3:
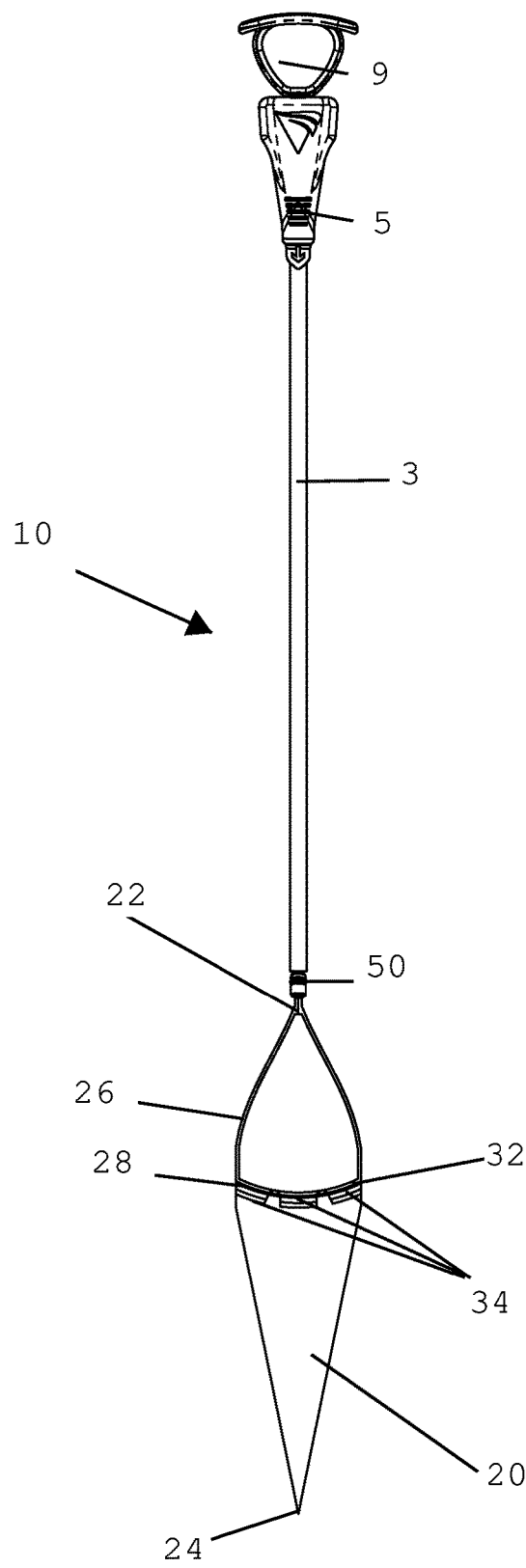
FIG. 3 is a top view of the tissue retrieval system of FIG. 1 with the retrieval bag deployed.

With reference to FIGS. 2 and 3, the tissue retrieval system can include a retrieval bag 20 that is deployable from the distal end of the introducer 3 which can be used as a receptacle for tissue specimens. After insertion of tissue specimens into the retrieval bag 20, the retrieval bag can then be cinched closed to prevent spillage of its contents and to prevent contamination of the body cavity and body cavity wall during withdrawal of the retrieval bag 20 from within the body cavity.

Figure 4A:
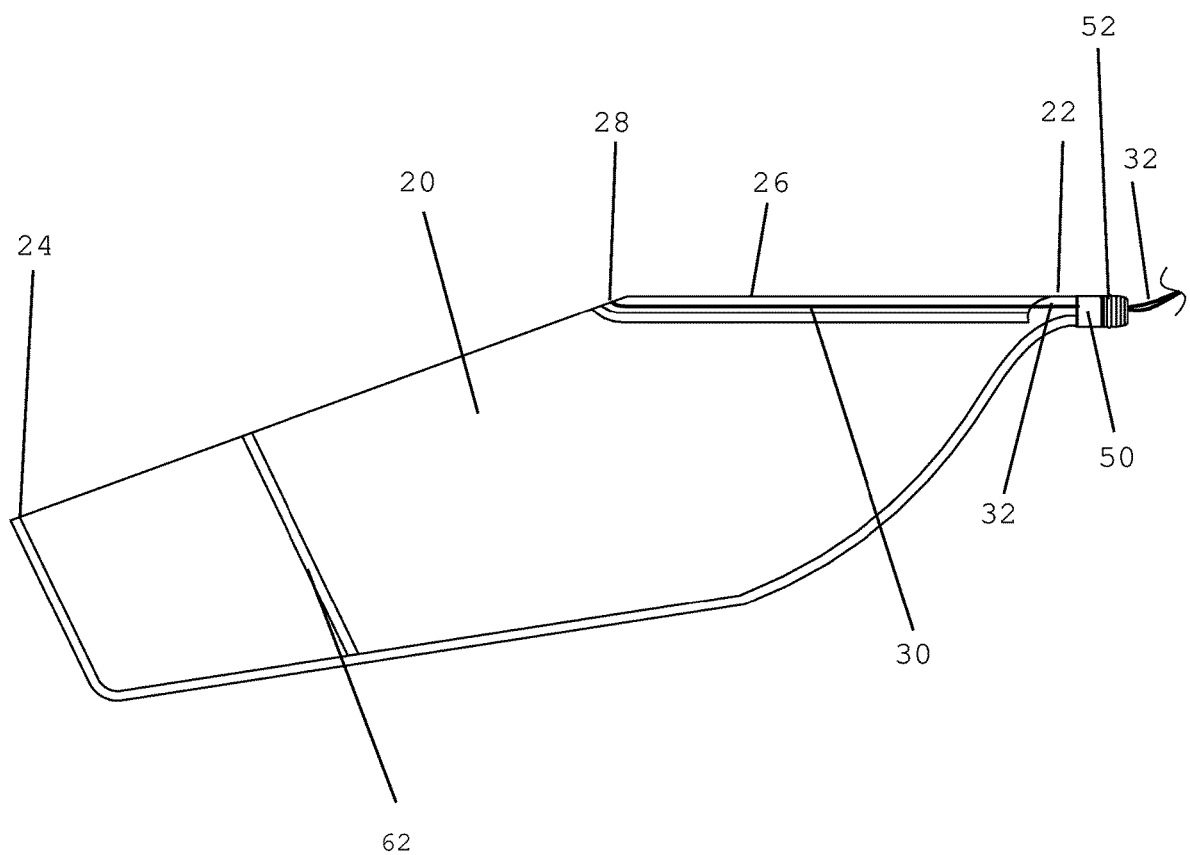
FIG. 4A is a side view of the tissue retrieval bag of the tissue retrieval system of FIG. 1.

With reference to FIGS. 2, 3, and 4A, in some embodiments, the tissue retrieval system includes a retrieval bag 20 sized and configured to be contained within a relatively small (such as, for example, a 5-7 mm) diameter introducer tube while providing a retrieval bag with a similar size and volume as laparoscopic retrieval bags for use with 10 mm trocars. Advantageously, such a retrieval bag 20 can facilitate various laparoscopic surgical procedures with the use of relatively small single incision site surgical access points.

With continued reference to FIGS. 2, 3, and 4A, in the illustrated embodiment, the tissue retrieval bag 20 has a distal end 24 opposite a proximal end 22. The illustrated tissue retrieval bag 20 includes a rim 26 defining an opening adjacent the proximal end 22 into the tissue retrieval bag 20, while the distal and 24 of the tissue retrieval bag 20 is closed. Thus, in the illustrated embodiment, the tissue retrieval bag 20 has an elongate profile, with a portion of the tissue retrieval bag 20 extending distally from the rim 26 and the opening. The distally extending portion of the retrieval bag diverges at an angle transverse to the rim 26 of the bag 20.

Advantageously, this elongate profile allows the tissue retrieval bag 20 to have a relatively small outer diameter when in a stowed configuration (FIG. 1), while having a relatively large volume in a deployed configuration (FIGS. 2, 3, and 4A). Thus, the tissue retrieval bag 20, in the stowed configuration, can fit within a relatively small diameter introducer tube 3. With reference to FIG. 4A, in order to position the tissue retrieval bag 20 in the stowed configuration, the tissue retrieval bag 20 can be rolled about an axis generally parallel to a longitudinal axis defined by the rim 26 and the opening of the bag. Thus, in the stowed configuration, the distal end 24, and the distal-extending portion of the tissue retrieval bag 20 is positioned longitudinally distally of the rim 26 and the opening with respect to the axis defined by the rim 26. The tissue retrieval bag 20 in the stowed configuration can be stored within the introducer tube 3. The cross-sectional area at any point along the length of the rolled retrieval bag with respect to the longitudinal axis defined by the rim 26 is equivalent to or smaller than the cross-sectional area of a relatively small introducer tube, such as a 5-7 mm introducer tube. Likewise, the cross-sectional area at any point along the axis of the rolled retrieval bag 20 is decreased as compared to prior retrieval bags of approximately the same volume.

In one embodiment, the tissue retrieval bag 20 is sized such that the volume of the retrieval bag is approximately 180 mL and the tissue retrieval bag 20 in the stowed configuration fits within a 5-7 mm trocar introducer. In some embodiments, the volume of the tissue retrieval bag is greater than approximately 100 mL. Accordingly, a ratio of the volume of the retrieval bag to its stowed diameter can be relatively high, in the exemplary embodiment, approximately 26-36 mL/mm. In other embodiments, the tissue retrieval bag 20 can be sized such that the volume is between about 50 mL and 400 mL, desirably between about 100 mL and 350 mL, and more desirably between about 150 mL and 200 mL. In some embodiments, the volume of the retrieval bag 20 fit within a predetermined size trocar can be increased by further elongating the bag to enable a greater amount of tissue to be placed within the bag. For example, some embodiments of tissue retrieval bag for placement within a 5-7 mm trocar introducer can have a first length between the proximal end 22 and the distal end 24 and a first volume, while other embodiments of tissue retrieval bag for placement within a 5-7 mm trocar introducer can have a second length between the proximal end 22 and the distal end 24 and a second volume, where the first length is smaller than the second length and the first volume is smaller than the second volume.

In one embodiment, the retrieval bag 20 is configured from 4.2 mil (0.0042") thick polyurethane film. In some embodiments, the thickness of the polyurethane film can be greater than or less than 4.2 mil, such as, for example for use in extracting tissue of a relatively high or low weight. In some embodiments, the retrieval bag can be formed from a variety of materials including polyurethane, polyethylene, polyimide, ripstop Nylon®, polyester, and Mylar®. In some embodiments, the retrieval bag can be formed from laminated materials such as polyurethane coated ripstop Nylon, silicone coated ripstop Nylon, polyurethane coated ripstop polyester, silicone coated ripstop polyester, polyurethane coated taffeta, and polyurethane coated spandex. The thicknesses of any of these materials can be chosen based, at least partially, on considerations of tissue weight to be carried by the tissue retrieval bag and outer diameter of the tissue retrieval bag in a stowed configuration.

As further discussed below with respect to FIGS. 7-15, in some embodiments, the tissue retrieval bag 20 can have hybrid properties—that is material properties that vary from the open end of the bag to the closed end of the bag. For example, in some embodiments, the tissue retrieval bag 20 can be formed with two different thicknesses of the same film material. For example, a portion of the tissue retrieval bag 20 adjacent the distal end of the retrieval bag can be formed with a relatively thick film and have a relatively low compliance while the remainder of the retrieval bag can be formed with a thinner film and have a relatively higher compliance. By incorporating a film with an increased thickness in the distal portion of the retrieval bag, the tensile and burst strengths of the retrieval bag can be increased, or a tissue retrieval bag having equivalent tensile and burst strengths can have a smaller outer diameter in the stowed configuration.

In some embodiments, the tissue retrieval bag can be formed with two different materials. For example, a portion of the tissue retrieval bag adjacent the distal end can be formed from one material having a relatively high tensile strength while the remainder of the retrieval bag can be formed from a different material having a relatively lower tensile strength. For example, the distal portion of the retrieval bag can be formed from a polyurethane and ripstop Nylon laminate while the remainder of the retrieval bag can be formed from a polyurethane film. In some embodiments, the material utilized for the distal tip of the retrieval bag can have an increased thickness as compared to the material utilized for the remainder of the retrieval bag. By incorporating different materials in different areas of the retrieval bag, the tensile and burst strengths of the retrieval bag can be increased, or a tissue retrieval bag having equivalent tensile and burst strengths can have a smaller outer diameter in the stowed configuration.

With reference to FIGS. 2, 3, and 4A, the tissue retrieval bag can include a non-continuous cuff 30 for retaining a cord 32 that is used for cinching the retrieval bag closed and for withdrawing the retrieval bag 20 through a body wall. During withdrawal of the retrieval bag 20 through a body wall, tensile stresses are concentrated at the distal portion 28 of the rim 26. This concentration of stresses can be especially pronounced in the withdrawal of the retrieval bag 20 through a relatively small diameter incision or access device. Therefore, in some embodiments, it can be desirable to provide the retrieval bag 20 with a reinforced distal cuff 30 having a reinforced section at a distal portion 28 of the rim 26 or opening. The cuff 30 can include one or more loops 34 formed at the distal portion 28 of the rim 26 for retaining the cord 32. The loop 34 can consist of a single layer of film, or can comprise multiple layers of film to provide the retrieval bag with a reinforced cuff. The number of layers and thickness of each layer can be sized to provide a predetermined tensile strength for the retrieval bag. In other embodiments, it can be desirable that the retrieval bag is formed with a continuous cuff rather than a reinforced cuff 30 with one or more layers of loops 34 such that the cuff is substantially continuous through the distal portion of the retrieval bag 20.

Figure 7:
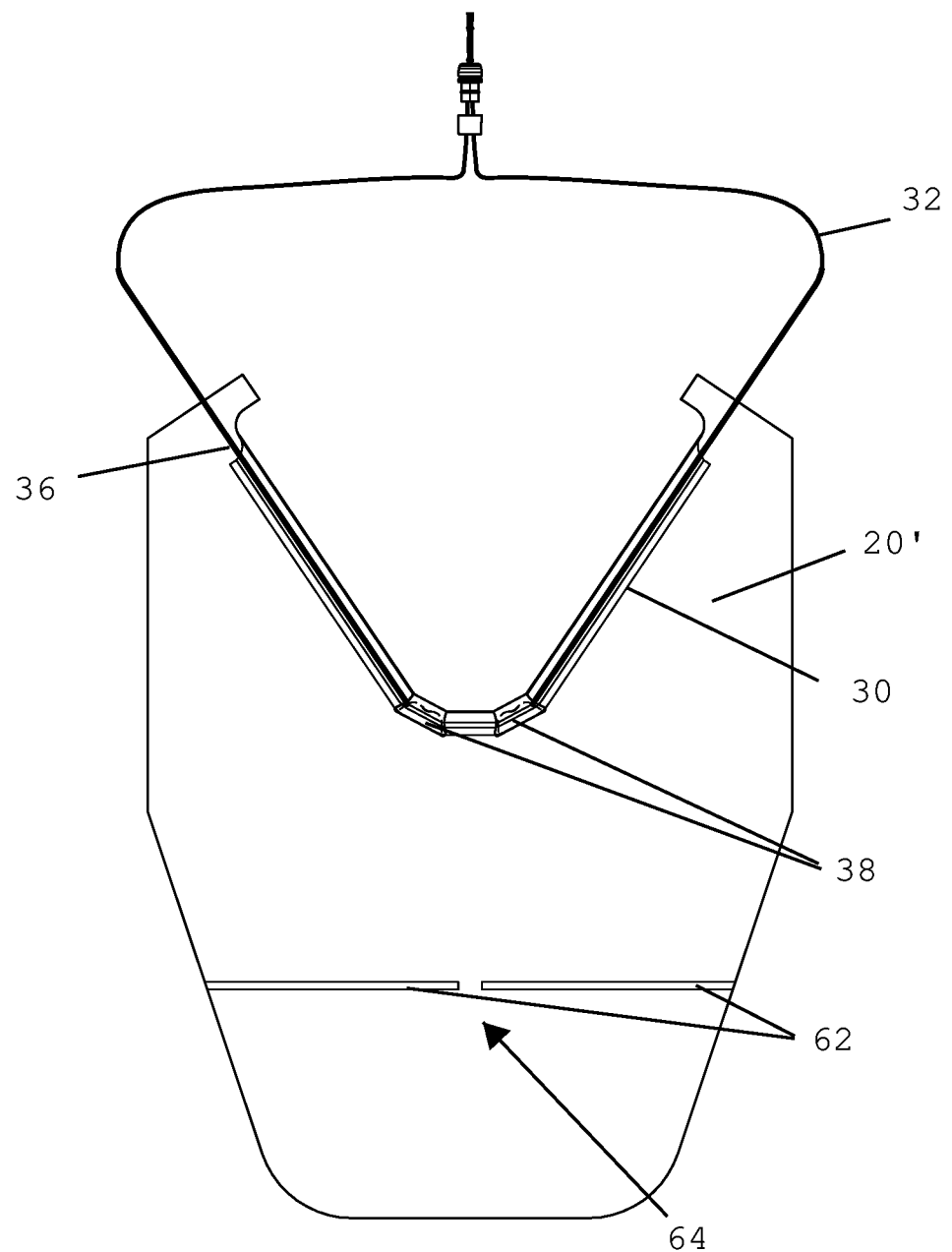
FIG. 7 is a top view of an embodiment of tissue retrieval bag having an elongate profile and hybrid construction in a partially-formed state.
Figure 8:
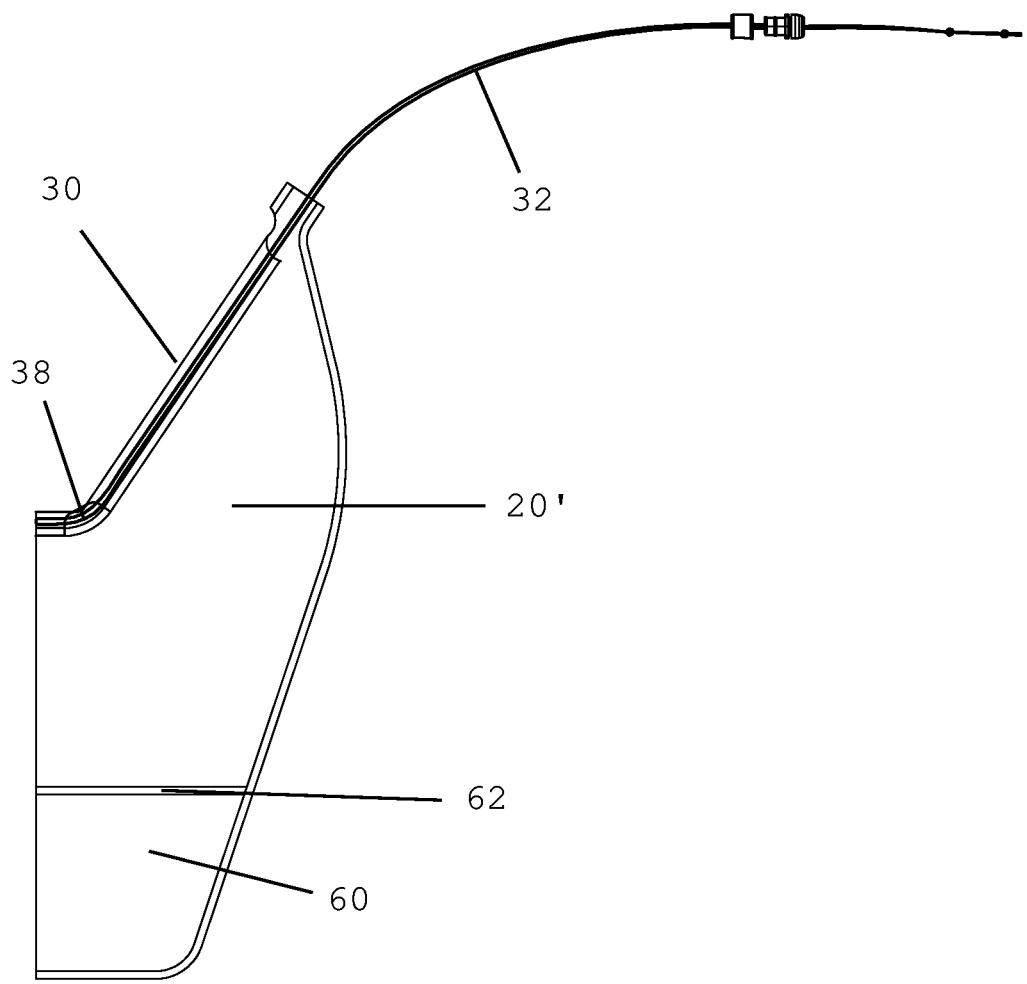
FIG. 8 is a side view of the tissue retrieval bag of FIG. 7 in a fully-formed state.
Figure 9:
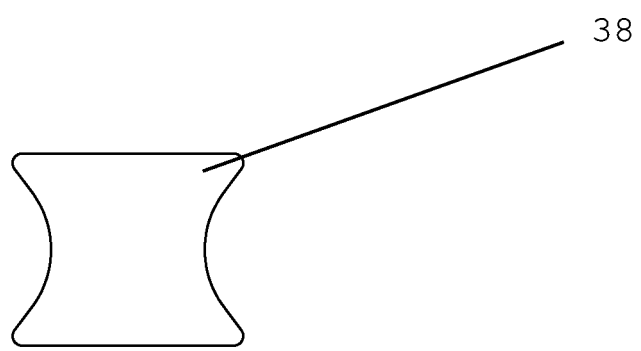
FIG. 9 is a top view of an embodiment of cuff reinforcement tab for the tissue retrieval bag of FIGS. 7-8.

With reference to FIGS. 7-9, an embodiment of tissue retrieval bag 20' is illustrated combining several aspects of tissue retrieval bags discussed herein. FIG. 7 illustrates the tissue retrieval bag 20' in a partially formed state illustrating partial assembly of the bag from a flat sheet of a film before a closed end of the bag has been formed such as by welding. FIG. 8 illustrates the tissue retrieval bag 20' in an assembled state with a sealed closed end. In the illustrated embodiment, the tissue retrieval bag 20' includes a distal end that has been reinforced with a reinforcing section 60 joined to the remainder of the bag 20' at a seam 62. For example, in one embodiment, the retrieval bag 20' can comprise a 4 mil film, and the reinforcing section can comprise, for example, a second layer of film material having a thickness of 2 mil for a total 6 mil thickness at the reinforcing section. As discussed in further detail with respect to FIGS. 10-13, the seam 62 can include a space or gap 64 therein to provide a vented cavity between the reinforcing section 60 and ambient conditions.

With continued reference to FIGS. 7-9, In the illustrated embodiment, the cord loop 32 passes through a cuff 30 at an opening 36 in the cuff 32. The cuff 30 can be formed in a flat sheet of film material by folding a portion of the film material over itself and joining the folded portion to the remainder of the material such as by welding. Desirably, the cuff 30 can be formed with the cord loop 32 in place. In the illustrated embodiment, the cuff is substantially continuous, as it includes a plurality of reinforcing tabs 38 joined to the cuff 30 to provide enhanced strength for a portion of the cuff encountering a relatively high tensile stress during use. Desirably, at least one reinforcing tab 38 can be added to the cuff 30 to form a reinforced section of the cuff 30. In the illustrated embodiment, two reinforcing tabs 38 are joined to the cuff 30 to reinforced the distal-most end of the cuff. In other embodiments, more or fewer than 2 reinforcing tabs can be added to the cuff to form a cuff having the desired level of continuity and reinforcement.

A detail view of one reinforcing tab 38 is illustrated in FIG. 9. In the embodiment illustrated in FIG. 9, the reinforcing tab 38 is formed from a segment of a film material having a substantially hourglass shape. Advantageously, such a geometry can facilitate folding and rolling of the tissue retrieval bag 20' to a relatively low diameter configuration for installation in a trocar. In other embodiments the cuff tab can have different geometries, such as substantially rectangular or oval geometries to create a cuff having desired strength and stowage properties.

Certain aspects of the retrieval bag described herein for use with 5-7 mm trocars can also be adapted to be used with 10 mm and larger diameter trocars. In this case, the diameter of the introducer tube would be approximately 10 mm, such as, for example, 10-12 mm. For example, a tissue retrieval system with an approximately 10 mm introducer tube can include a tissue retrieval bag having elongate profile comprising a film thickness of approximately 8 mils. Advantageously, such a tissue retrieval bag with an elongate profile has enhanced tensile and burst strength characteristics as compared to prior 10 mm retrieval bags.

In other embodiments of tissue retrieval system for use with 10 mm and larger diameter trocars, a tissue retrieval bag can be configured to have a relatively large volume, rather than enhanced strength as compared to prior 10 mm retrieval bags. For example, in some embodiments, an elongate profile of a tissue retrieval bag configured for use with 5-7 mm trocars can be generally scaled up in size, but not film thickness, to be used with 10 mm and larger diameter trocars. Thus, the resulting tissue retrieval bag would fit within a 10 mm introducer tube and have an increased volume relative to prior 10 mm tissue retrieval bags to accommodate a large tissue specimen, such as a spleen. In other embodiments, the dimensions and film thickness of a tissue retrieval bag for use with a 10 mm or larger diameter trocar can each be selected such that the tissue retrieval bag has desired volume and strength characteristics.

In some embodiments, the tissue retrieval system can be provided with a 15 mm introducer tube and incorporate a larger version of a tissue retrieval bag having the elongate profile of the 5 mm retrieval bag described above. In some embodiments, the 15 mm retrieval bag could also incorporate film materials with greater thicknesses than those utilized for the 5 mm retrieval bags, or some combination of an elongate profile and varied film thickness.

Figure 5:
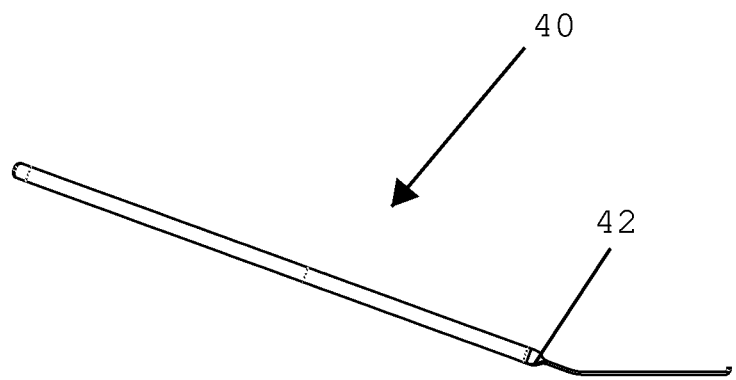
FIG. 5 is a side view of one support arm of the tissue retrieval system of FIG. 1.
Figure 6:
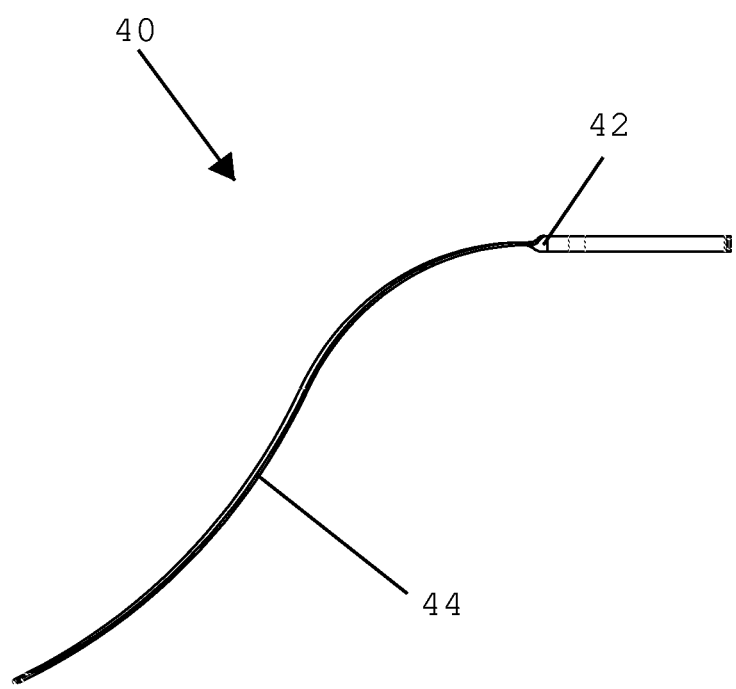
FIG. 6 is a top view of the support arm of FIG. 5.

With reference to FIGS. 2, 5, and 6, in some embodiments, the tissue retrieval systems 10 described herein include retrieval bag support arms 40 which are biased to a predetermined position when the tissue retrieval system is in the deployed configuration. For example, in the illustrated embodiment, the support arms 40 are biased to spring radially outward and transversely upward with respect to a longitudinal axis defined by the introducer 3 upon deployment of the retrieval bag 20 from the introducer 3. Desirably, by springing transversely upward upon deployment of the retrieval bag 20, the support arms create an access position having an angled entry for the rim 26 of the retrieval bag 20 relative to the axis of the introducer 3. Advantageously, the angled entry facilitates the loading of tissue specimens during laparoscopic procedures as it allows a grasped tissue sample to be easily disposed within the retrieval bag 20. This ease of loading can be particularly advantageous for single incision laparoscopic procedures where the grasped tissue is held by a grasper that is disposed through the same incision as the retrieval system introducer 3. Thus, the transverse orientation of the retrieval bag 20 rim 26 relative to the longitudinal axis of the introducer 3 enables a tissue specimen held by a grasper to be easily inserted and pushed towards the distal end 24 of the retrieval bag 20 during single incision laparoscopic procedures where it would otherwise be particularly difficult to create a substantial axial angle between the grasper shaft and the introducer tube.

With continued reference to FIGS. 2, 5, and 6, in some embodiments, a tissue retrieval system can include support arms 40 designed to flex open and upward upon deployment of the retrieval bag 20 from within the introducer 3 tube to facilitate the loading of a tissue specimen sample during standard laparoscopic procedures and during single incision laparoscopic procedures. As illustrated, the support arms 40 can be bent to include upward bends 42 in each support arm 40 in the sections of the support arms that are proximal to where a bead 50 is positioned and distal to the end of the actuation rod. When viewed from a top perspective, as illustrated in FIG. 6, each of the support arms 40 can also include a radial bend, curve, or curved profile 44. As the retrieval bag 20 is advanced out of the introducer 3, the support arms 40 spring radially outward to return to the radial curved profile 44, thus opening the retrieval bag. As the retrieval bag 20 is further advanced out of the introducer 3, the support arms 40 spring upward about the bends 42 in the support arms 40 to position the retrieval bag 20 in the access position with an angled opening relative to the longitudinal axis of the introducer 3. As the retrieval bag 20 is cinched closed, the support arms 40 flex downward and radially inward as they are retracted into the introducer 3.

In some embodiments, the support arms 40 can be formed from 17-7 PH stainless steel, which is a typical spring metal. In other embodiments, the support arms 40 can comprise other metals and metal alloys having desired biasing properties. In other embodiments, the support arms 40 can be formed of a memory metal such as a nickel titanium alloy or nitinol metal. The memory metal can be preshaped to be generally linear in the introducer 3 with the tissue retrieval system in the initial configuration and to form a radially expanded and transversely bent shape upon application of body heat to the support arm 40 as the tissue retrieval bag 20 is deployed into a body cavity.

Instead of, or in addition to the biased support arms 40 discussed above, in some embodiments, the support arms can pivot about a pin and the tissue retrieval system can include a torsion spring to drive the support arms upward upon deployment from the introducer tube. This spring-biased pivot mechanism can provide the retrieval bag with an angled opening relative to the longitudinal axis of the introducer tube.

During clinical use of the tissue retrieval systems described herein, an access device such as a trocar is first placed through a body wall leaving the trocar cannula disposed across the body wall. In some embodiments, it is contemplated that a would retractor, such as an Alexis® would retractor can be positioned in an incision in the patient's body before placement of the trocar cannula. In these embodiments, a wound retractor is initially inserted into an incision. Then, any adjustments to the length or diameter of the wound retractor are made. For example, with certain wound retractors, an external ring of the retractor can be rolled to remove slack in an elastomeric sheet forming the wound retraction surface.

The tissue retrieval system 10 is then inserted into the trocar seal and cannula until the distal end of the introducer 3 extends beyond the distal end of the trocar cannula. The retrieval bag 20 is then deployed from within the introducer 3 and into the body cavity by pushing the actuator 7 in a distal direction relative to the introducer 3. In some embodiments of tissue retrieval system, the actuator rod can include a ratcheting mechanism which allows distal movement of the actuator 7 during retrieval bag deployment and prevents the actuator 7 from being pulled in a proximal direction to ensure proper operation of the device. Once extended into the body cavity, the retrieval bag 20 is suspended and held open by two support arms 40 that extend into the cuff 30 on the retrieval bag 20.

The retrieval bag 20 can include an integral bead 50 through which the support arms 40 can slide. The retrieval bag 20 also includes a cord loop 32 which runs through the cuff 30 of the retrieval bag 20 and is releasably attached to the actuator 7. In some embodiments, the bead 50 includes a frictional lock through which the cord loop 32 runs to enable the retrieval bag 20 to be cinched closed and reopened as needed. Various aspects of an introducer and guide bead that can be used in conjunction with the various retrieval bags 20, 20', 20" described herein are further described in U.S. patent application Ser. No. 11/549,971 entitled "TISSUE RETRIEVAL SYSTEM," filed on Oct. 16, 2006, currently pending, which is incorporated herein by reference in its entirety.

With reference to FIG. 4A, an some embodiments, the bead 50 can include an expandable, relatively large diameter member such as a snap ring 52 positioned about a periphery thereof. In the illustrated embodiment, the snap ring 52 can prevent reentry of the guide bead 50 into the introducer 3 once the actuator 7 has advanced the retrieval bag 20 and guide bead 50 out of the introducer, thus facilitating cinching of the retrieval bag 20 when the cord 32 is pulled. In other embodiments a portion of bag material adjacent the guide bead 50 can facilitate cinching of the retrieval bag 20. For example, in these embodiments, the guide bead 50 can be pulled within the introducer 3 tube while the tissue retrieval bag 20 can collect and bunch up outside the introducer 3 tube when the cord is pulled.

With reference to FIGS. 4B, 4C, and 4D, in some embodiments, introducer 3 can have a distal end configured to allow passage of the guide bead 50 during deployment of the retrieval bag 20 while also restricting reentry of the deployed guide bead 50 into the introducer 3. In the illustrated embodiment, the distal end of the introducer 3' can comprise at least one restrictor such as one or more generally vee-shaped ramped surfaces 13. In the illustrated embodiment, the introducer 3' includes two generally diametrically opposed ramped surfaces 13. In certain other embodiments, the introducer 3' can have more or fewer than two ramped surfaces, and the ramped surfaces can be generally regularly spaced about the periphery, or can be irregularly spaced. The ramped surfaces can define a gradually decreasing inner diameter of the introducer 3' to a relatively low diameter region 15 minimum inner diameter at the distal end. Desirably, the ramped surfaces 13 extend a relatively short distance in a longitudinal direction such that the ramped surfaces 13 do not interfere with movement of the actuator 7. In some embodiments, the guide bead 50 can include an interface surface, such as a diametric step 54 to interface with ramped surfaces 13 of the introducer 7. Advantageously, in the illustrated embodiment, the ramped surfaces 13 facilitate easier passage of the rolled retrieval bag 20 through the introducer 3' while preventing reentry of the guide bead 50 to cinch the retrieval bag 20.

Once a tissue specimen such as a gallbladder is separated from the adjoining vessels and structures, it can then be placed into the retrieval bag 20. The actuator 7 is then pulled proximally to withdraw the support arms 40 from the cuff 30 and the bead 50 on the retrieval bag 20. The actuator 7 can include a ratcheting mechanism which allows proximal movement of the actuator 7 during cinching of the retrieval bag 20 and prevents distal movement of the actuator 7 to ensure proper and complete closure of the retrieval bag 20. As the support arms 40 are pulled out of the cuff 30 of the retrieval bag 20 and through the bead 50, tension is then applied to the cord loop 32 to cinch the bag 20 closed. Once the retrieval bag 20 is fully closed, a small loop of the cord 32 is exposed on the actuator 7 near the proximal end of the introducer 3.

At this stage, there are at least three methods for withdrawal of the retrieval bag 20 from within the body cavity. For one method, the retrieval bag 20 can be completely detached and removed from the actuator 7 and introducer 3 by lifting the cord loop 32 from a retaining feature such as a retaining slot on the actuator 7. The device and the trocar seal and cannula can then be withdrawn from the body wall leaving the retrieval bag 20 in the body cavity and the cord loop 32 disposed across the body wall. The neck of the retrieval bag 20 can then be withdrawn through the body wall using the bead 50 as a dilator to aid with movement of the retrieval bag through the layers of tissue fibers in the body wall. Once the neck of the retrieval bag 20 has traversed the body wall, the retrieval bag can then be reopened by manually grasping the closed end of the retrieval bag 20 and the bead and sliding the bead 50 along the cord 32. The retrieval bag 20 can then be accessed to remove or compact its contents to aid with complete withdrawal from the body cavity using standard open and endoscopic instrumentation such as forceps, graspers, and aspiration probes. Once the bulk of the contents are removed, the retrieval bag 20 can then be closed by manually grasping the open end of the retrieval bag 20 and the bead and sliding the bead 50 along the cord 32. The cord loop 32 can then be grasped manually and the retrieval bag 20 then completely withdrawn from the body cavity.

A second method for withdrawal of the retrieval bag 20 from within the body cavity can be used for small tissue specimens placed in the retrieval bag 20 which are not likely to need to be aspirated, compacted, or removed from the retrieval bag 20 prior to withdrawal of the retrieval bag 20 through the body wall. In this case, the cord loop 32 can be left attached to the actuator 7 and the entire device along with the trocar seal and cannula can be simultaneously withdrawn from the body cavity and through the body wall.

In a third method, the tissue retrieval systems described herein can be used in conjunction with a wound retractor such as an Alexis® retractor, as discussed above. A method of using a tissue retrieval system in conjunction with a wound retractor includes first inserting a small wound retractor in the wound that would be lightly tensioned such as by inverting an external ring of the wound retractor to remove slack in the wound retractor sleeve. A trocar is then inserted within the sleeve of the wound retractor into the lined incision. A tissue retrieval system, such as one of the embodiments discussed herein would be inserted through the trocar and deployed. A tissue specimen is placed in the deployed bag. Once the specimen is placed in the tissue bag, the bag is cinched closed. In certain embodiments described herein, the cord loop can be detached from the actuator. With the bag cinched closed about a specimen contained therein, the introducer tube can be removed from the bag. In some embodiments, the trocar can also removed from the surgical site. The wound retractor is then fully tensioned to retract the wound to facilitate removal of the tissue bag from the body cavity such as by inverting an external ring to fully retract the incision site. With the incision site fully retracted, the retrieval bag described herein can be pulled through the wound retractor and out of the patient. Advantageously, a wound retractor can allow a tissue retrieval bag to be pulled through a relatively small incision without requiring the incision to be extended for passage of the bag therethrough.

The tissue retrieval bags 20 described herein can be utilized as stand alone retrieval bags that would be delivered to the surgical site through a trocar by rolling the retrieval bags and then pushing or pulling them through a trocar. A retrieval bag 20, in this aspect, would be provided with a cord loop 32 and can also be provided with a guide bead 50 or alternatively a slip knot for cinching the bag 20 closed. The reinforced distal section of the rim 26 of the retrieval bag 20 can allow the distal portion of the retrieval bag cuff 30 to remain in an open position without the need for metal or plastic supports. This version of the retrieval bag can be delivered through various trocars ranging in diameter from 5-15 mm. The stand-alone retrieval bag 20 could be formed from thick laminate materials to enable the use of tissue morcellators to be utilized for reducing the size of large tissue specimens such as the spleen. The elongate profile of the retrieval bag 20 facilitates the insertion and use of a tissue morcellator within the retrieval bag and is particularly advantageous during single incision laparoscopic procedures. The elongate profile retrieval bag also enables the retrieval bag 20 to be delivered to and fit within confined surgical sites due to its low profile shape.

With reference to FIGS. 10-15, various embodiments of hybrid tissue retrieval bags 20" are illustrated. Rather than being formed of materials having substantially uniform properties extending along the retrieval bag between an open end and a closed end, in various embodiments, the hybrid specimen retrieval bags have at least two portions with different properties (such as, for example, compliance, thickness, or number of layers of material), such that the bags are adapted for the clinical environment in which they are deployed. As discussed above with reference to FIGS. 7-8, in some embodiments, a hybrid tissue retrieval bag 20' can have an elongate profile. In other embodiments, as illustrated in FIGS. 10-15, a hybrid tissue retrieval bag can have a profile that extends generally perpendicularly to a longitudinal axis of the introducer tube 3 between an open end and a closed end of the bag.

Tissue retrieval bags formed of a material with uniform properties throughout can create undesirable stress concentrations in use. Retrieval bags typically have a large diameter opening in the cuff portion to facilitate insertion of a specimen and a smaller diameter of the distal closed-end of the retrieval bag. An exemplary uniform tissue retrieval bag with an internal diameter of about 2.75" and a wall thickness of about 4 mil in the cuff portion of the bag will experience a tensile stress of about 867 PSI in the cuff portion of the bag under tensile load of about 30 pounds. The same retrieval bag with an internal diameter of about 0.75" and a wall thickness of about 4 mil at the distal end of the bag will experience a stress of about 3166 PSI in the distal end of the bag under the same tensile load of about 30 pounds. The induced tensile stresses of the uniform-material retrieval bag in the cuff portion and the lower distal portions are not balanced due to the differences in their respective diameters. The induced tensile stress of 867 PSI in the cuff portion of the bag is relatively low compared to the induced tensile stress of 3166 PSI in the distal end of the bag. Thus, a substantially uniform non-hybrid bag can require a relatively high strength material or a relatively thick material throughout to provide a desired strength at the distal end even when such a material is not required at the cuff portion of the bag. Accordingly, it can be desirable that a specimen retrieval bag be configured to generate a more balanced stress response under tensile loads expected in clinical application.

Figure 10:
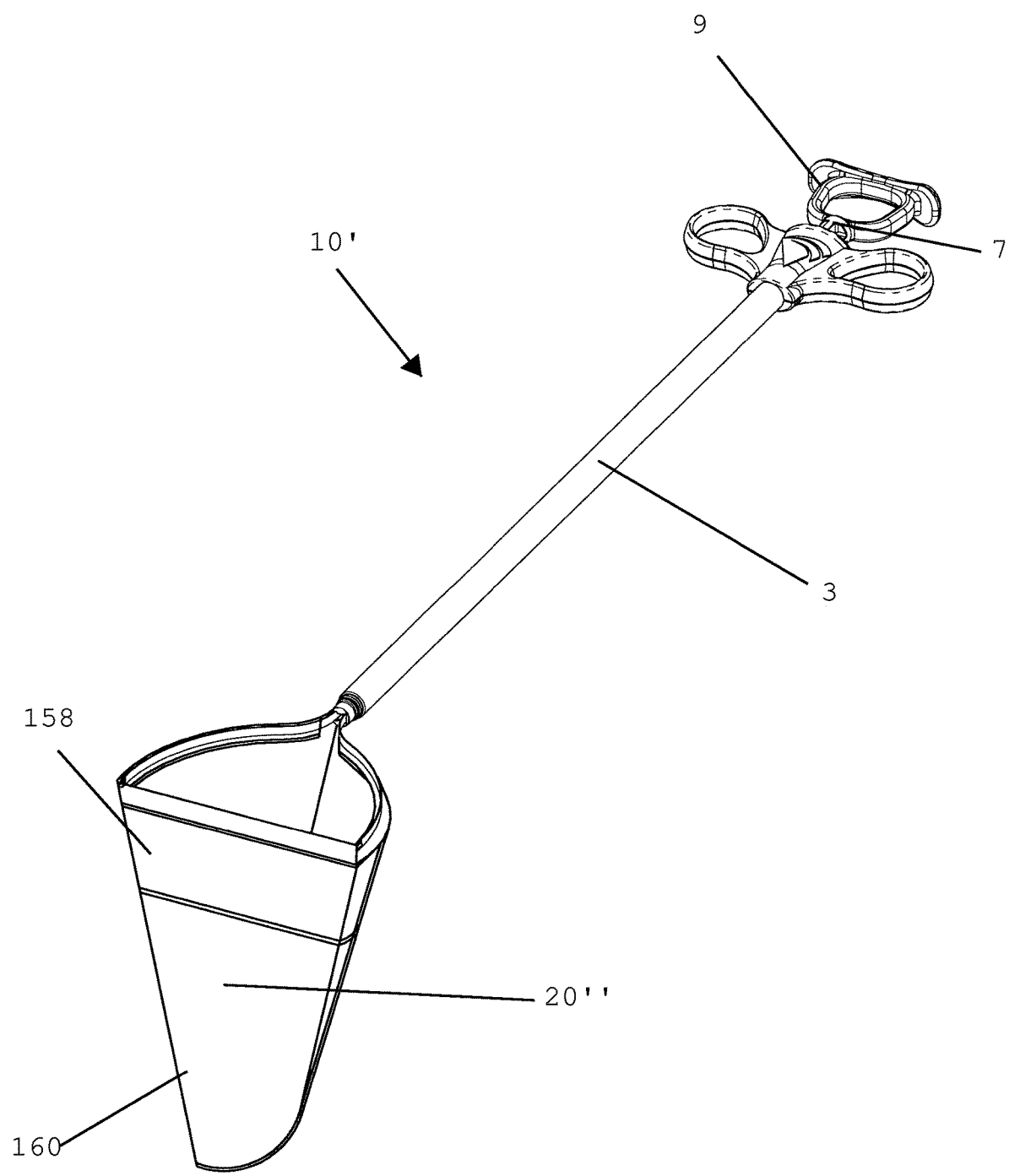
FIG. 10 is a perspective view of an embodiment of tissue retrieval system including an embodiment of hybrid tissue retrieval bag.

Thus, advantageously, in some embodiments, the tissue retrieval system can include a retrieval bag configured to provide enhanced strength at stress concentrations versus prior art retrieval bags. In some embodiments, the tissue retrieval system can include a "hybrid" retrieval bag 20" configured to provide localized areas of relatively high strength and localized areas of relatively lower strength and higher compliance. The hybrid retrieval bag can have localized areas of high strength in locations such as a distal, closed end and/or a distal end of the cuff, where tissue retrieval bags typically encounter relatively high stress. FIG. 10 illustrates an exemplary hybrid tissue retrieval bag 20" in a tissue retrieval system 10' including a handle 9, an actuator rod 7, and an introducer tube 3 for insertion through a trocar.

Figure 11:
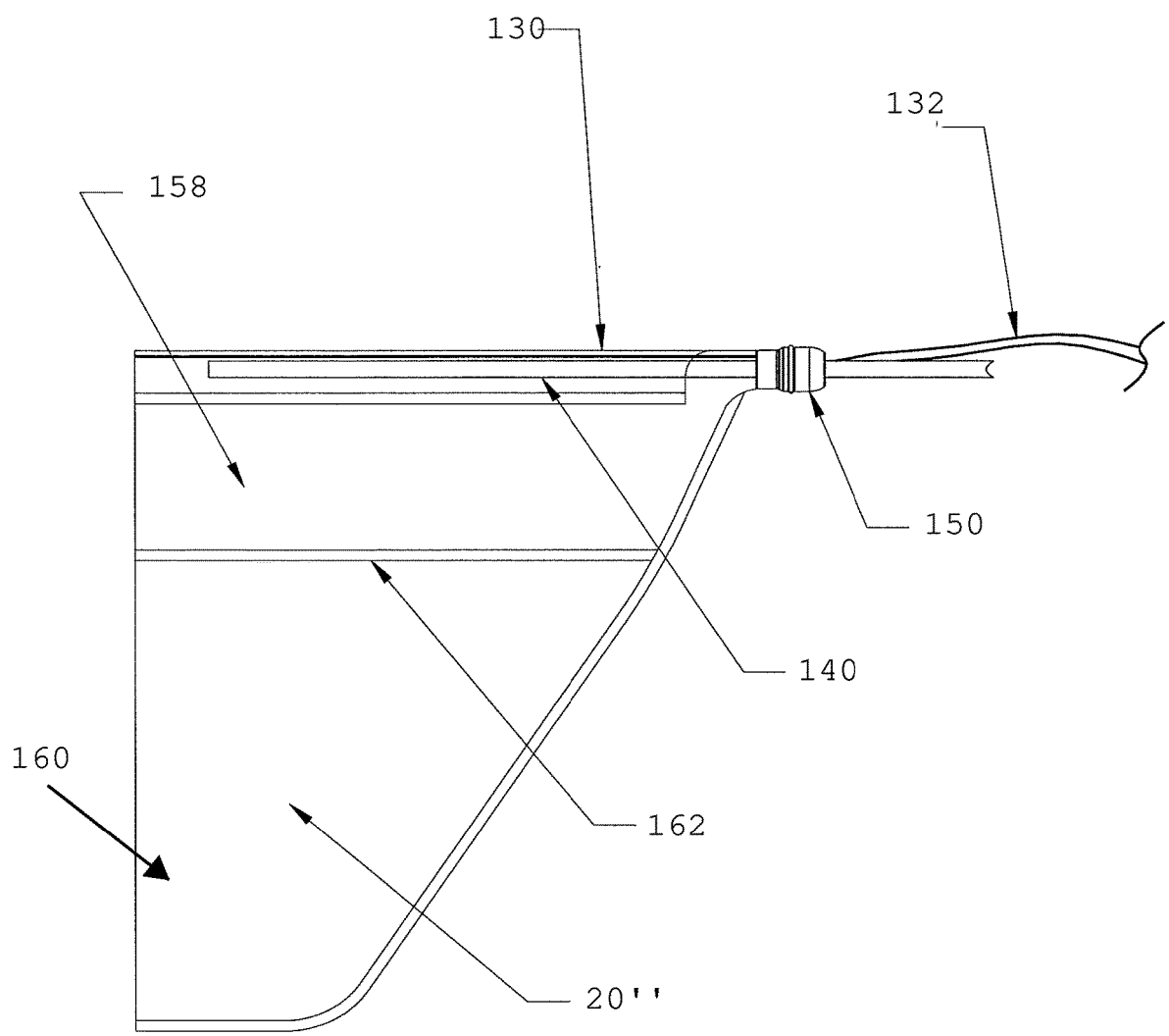
FIG. 11 is a side view of one embodiment of hybrid tissue retrieval bag.
Figure 12:
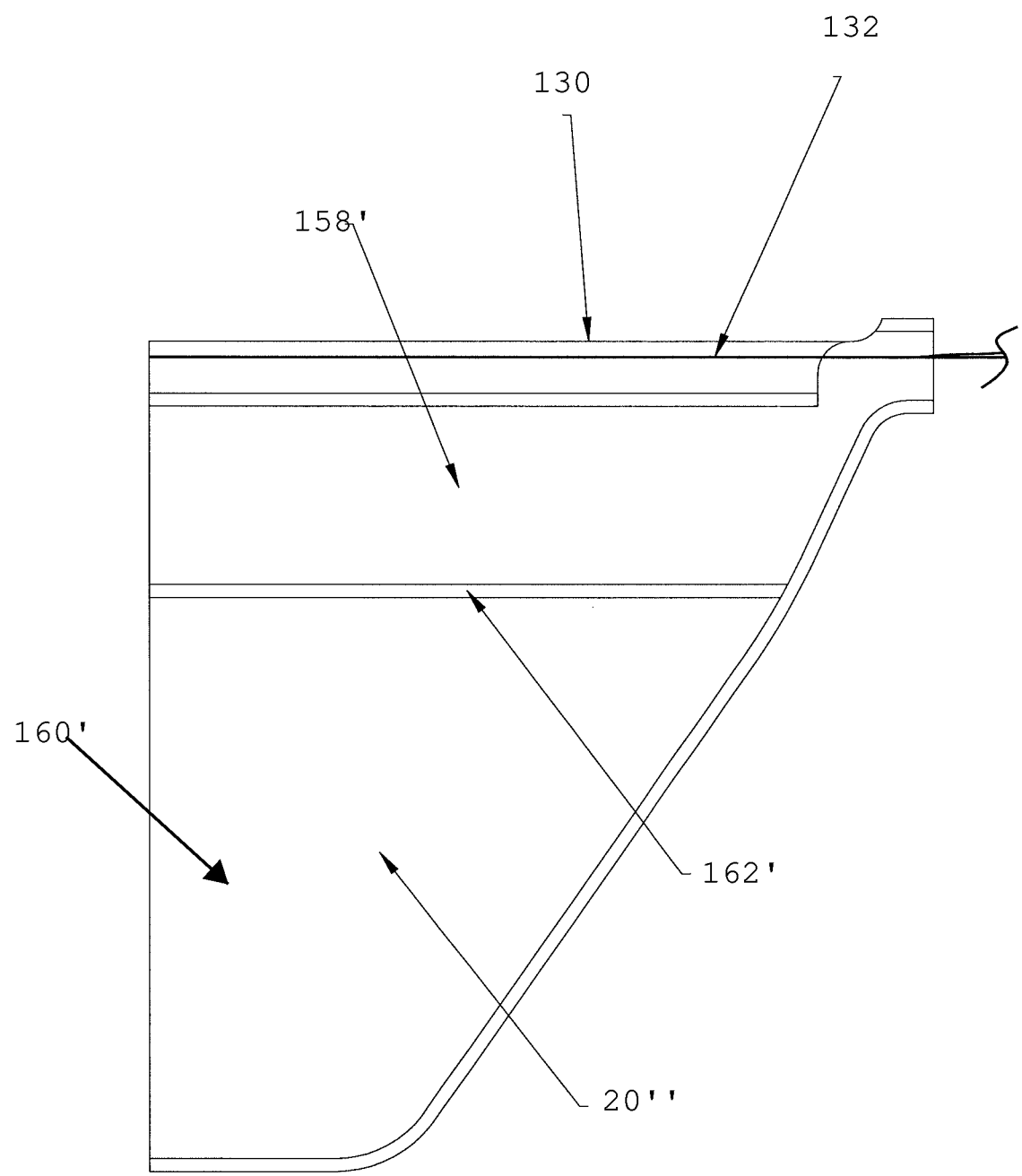
FIG. 12 is a side view of one embodiment of hybrid tissue retrieval bag.

With reference to FIG. 11, in some embodiments, a hybrid retrieval bag 20" can be formed of at least two different film materials to provide relatively high flexibility at the proximal open end of the retrieval bag 20" and relatively high strength at the distal closed-end of the retrieval bag 20". With reference to FIG. 12, in other embodiments, a hybrid retrieval bag 20" can be formed with at least two different thicknesses of the same film material. In some of these embodiments, the retrieval bag 20" can be formed with a relatively thin film in the proximal open end of the retrieval bag 20" to enhance flexibility while maintaining adequate strength and a relatively thick film in the distal closed-end of the retrieval bag 20" to enhance strength while enabling the retrieval bag 20" to be rolled and stored in the introducer tube 3.

In other embodiments, a hybrid retrieval bag 20" can be formed with at least two different thicknesses of at least two different film materials. In certain of these embodiments, the hybrid retrieval bag 20" can provide flexibility at the open proximal end of the retrieval bag 20" and strength at the distal closed-end of the retrieval bag 20" while enabling the retrieval bag 20" to be easily rolled and stored in the introducer tube 3.

Figure 14:
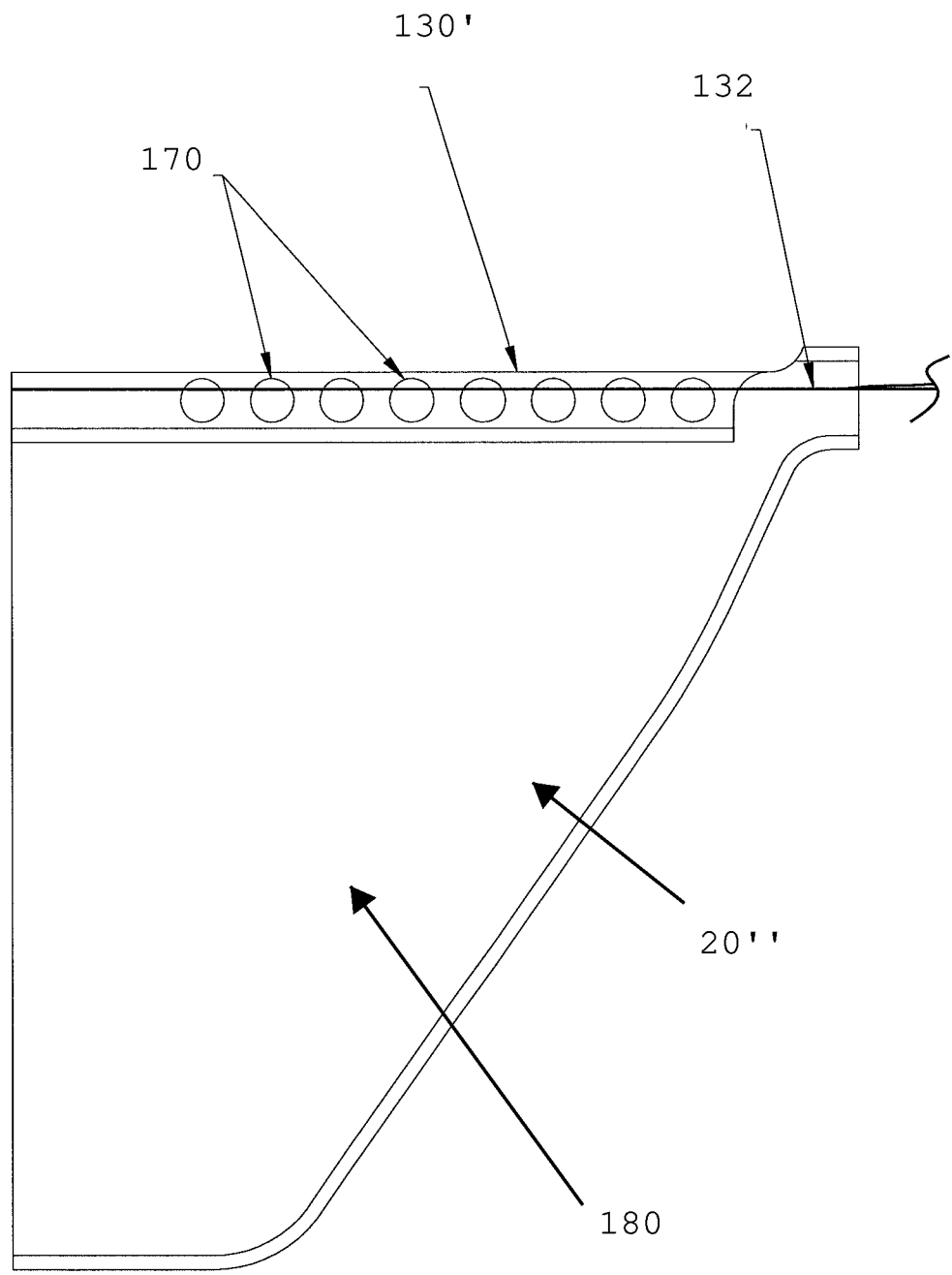
FIG. 14 is a side view of one embodiment of hybrid tissue retrieval bag.
Figure 15:
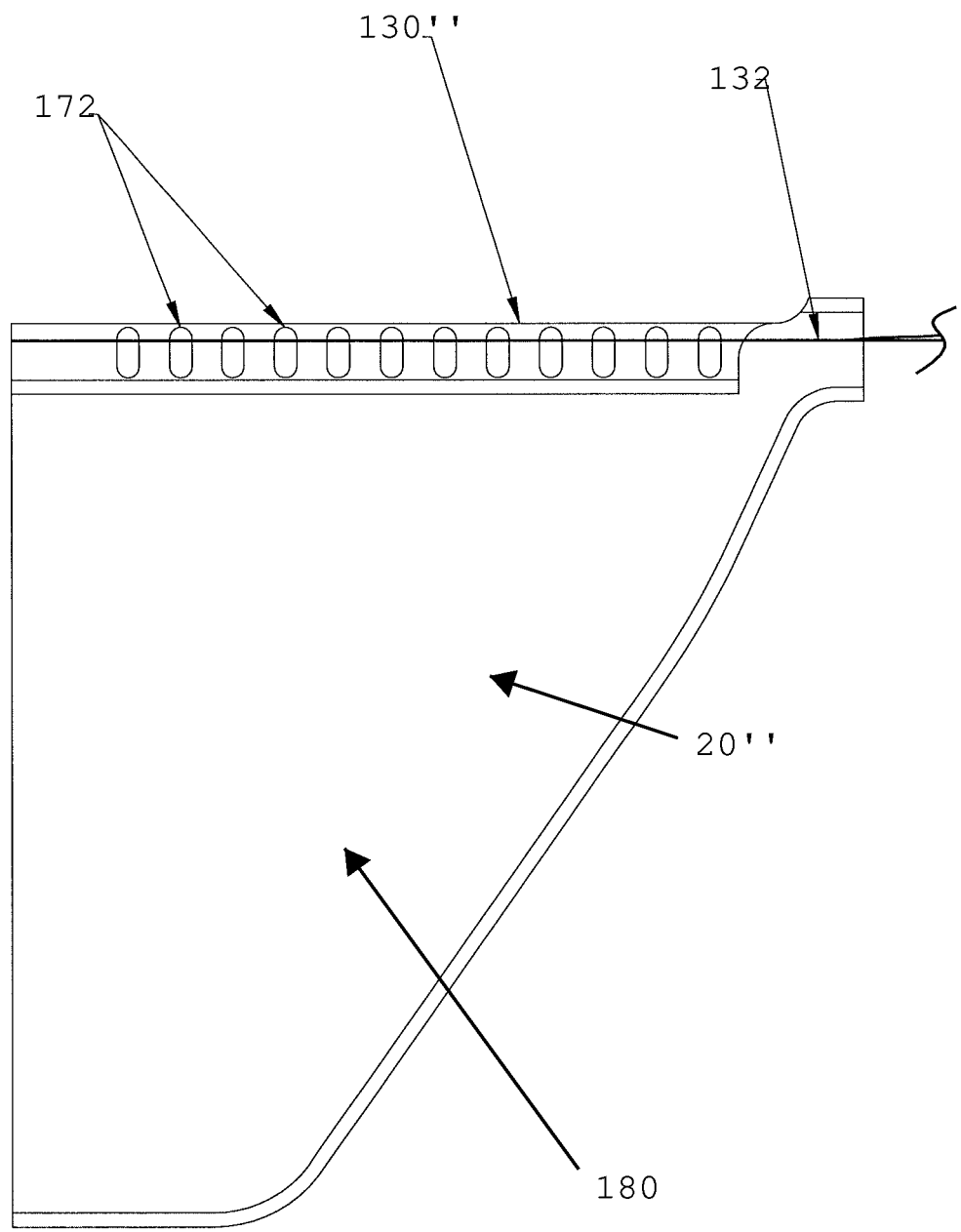
FIG. 15 is a side view of one embodiment of hybrid tissue retrieval bag.

With reference to FIGS. 14-15, in some embodiments, a hybrid retrieval bag 20" can be formed with one or more compliant features such as holes or slots in the cuff portion of the bag to provide the cuff with an increased degree of compliance. In these embodiments, a relatively stiff high-strength material can be used for forming the tissue retrieval bag 20".

One embodiment of hybrid retrieval bag 20" formed of two film materials is illustrated in FIG. 11. In the illustrated embodiment, the hybrid retrieval bag 20" formed from two film materials is advantageous in that a first film material with a relatively high elongation and low modulus can be used for the upper cuff portion 158 of the retrieval bag 20" and a second film material with a relatively low elongation and a high modulus can be used for the lower, distal end portion 160 of the retrieval bag 20". A high modulus material requires a greater amount of force or pressure to be applied to the material to produce a given amount of elongation as compared to a low modulus material. Thus, advantageously, in the illustrated embodiment, the tissue retrieval bag 20" will have relatively low elongation at the distal end portion 160, which, as discussed above, encounters relatively high tensile stress during clinical use.

By using a relatively high modulus film for the lower distal end portion 160 of the retrieval bag, the retrieval bag 20" will have a greater resistance to localized deformation and elongation than a comparable non-hybrid tissue retrieval bag. Thus, the hybrid configuration of the retrieval bag 20" contributes to the ability of the retrieval bag with a contained specimen to be easily withdrawn through the abdominal wall of the patient. The high modulus film material will not elongate as much as a low modulus film material and will therefore be less susceptible to deformation under the high tensile force that can be applied to the retrieval bag during withdrawal of the retrieval bag from that peritoneal cavity. Under the high tensile forces applied to the retrieval bag during withdrawal from the peritoneal cavity, a non-hybrid retrieval bag formed solely of low modulus film materials can significantly elongate and stretch until the retrieval bag deforms to take on a bulbous shape within the peritoneal cavity. Once a retrieval bag deforms to a bulbous shape, it can be difficult to remove the retrieval bag through the abdominal wall. In certain instances where a retrieval bag formed of a low modulus film has deformed, it can be required that the abdominal wall tract is enlarged to enable passage of the retrieval bag through the tract. In some cases, aspiration of some of the retrieval bag contents must be conducted with an irrigation/aspiration probe to enable passage of the retrieval bag through the abdominal wall tract.

Advantageously, a hybrid retrieval bag formed of a high modulus film material for the lower portion 160 of the retrieval bag 20" is less likely to deform than a comparable non-hybrid retrieval bag formed of a relatively low-modulus material. Furthermore, the hybrid retrieval bag 20" tends to force the contained specimen to elongate within the retrieval bag 20" and to conform to the shape of the retrieval bag 20" and thus facilitates withdrawal of the retrieval bag from the peritoneal cavity.

With continued reference to FIG. 11, one embodiment of retrieval bag 20" formed from two film materials includes an upper cuff portion 158 formed of a first film material and a lower, distal end portion 160 formed of a second film material having a different compliance and a different modulus than the first film material. In the illustrated embodiment, the upper cuff portion 158 has a depth toward the closed end of the bag that measures about 1.5" from the open end of the retrieval bag 20". In other embodiments, the upper cuff portion 158 can have different depths. For example in some embodiments, the upper cuff portion can have a depth within the range of about one half an inch to about three inches, in other embodiments, the upper cuff portion can have a depth between about one inch and about two and a half inches, and in other embodiments, the upper cuff can have a depth of between about one and a quarter inches and one and three quarters inches.

In various embodiments, tissue retrieval bags discussed herein can be sized for different tissue removal applications. For example, in the illustrated embodiment, the retrieval bag 20" can have a total depth between the open end and the closed end of approximately 5 inches, but in other embodiments, it can be desirable to have a retrieval bag with a total depth of less than 5 inches or greater than 5 inches. Accordingly, to account for dimensional differences in different sized bags, it can be useful to describe the depth of the upper cuff portion 158 in terms of a ratio with the total depth of the tissue retrieval bag 20". In some embodiments, the ratio of the depth of the upper cuff portion to the depth of the bag from the open end to the closed end is between about 1:10 and about 1:1.5, in other embodiments, the ratio of the depth of the upper cuff of the tissue retrieval bag to the total depth of the beg is between about 1:4 and about 1:1.8, and in other embodiments, the ratio of the depth of the upper cuff of the retrieval bag to the total depth of the tissue retrieval bag is between about 1:3 and about 1:2.

In the illustrated embodiment, the first film material, comprising the upper cuff portion 158 comprises a 0.004" or 4 mil polyurethane film material, although in different embodiments, different thicknesses of film can be used, such as, for example, a 2 mil film, 6 mil film, or film of another suitable thickness. Furthermore, while in the illustrated embodiment, the upper cuff portion 158 comprises a polyurethane material, in other embodiments, the first film material can comprise another suitable film material.

Film material properties are typically reported as modulus at 100% elongation of the film with modulus in the units of pounds per square inch or pascals. As illustrated, the first film material comprising the upper cuff portion 158 has a modulus of about 950 PSI at 100% elongation. In other embodiments, the modulus can be between about 500 PSI at 100% elongation and about 1300 PSI at 100% elongation. In still other embodiments, the modulus can be between about 750 PSI at 100% elongation and about 1100 PSI at 100% elongation. In other embodiments, the modulus can be between about 900 PSI at 100% elongation and about 1000 PSI at 100% elongation.

With continued reference to FIG. 11, the lower, distal or closed-end portion 160 of the retrieval bag 20" is formed of a second film material having a second compliance or modulus. As illustrated, the distal-end portion 160 of the retrieval bag 20" has a depth measuring about 3.5" from the interface or joint 162 with the upper cuff portion 158 of the retrieval bag to the closed end of the bag 20". In other embodiments, the distal-end portion of the bag can have a depth of between about 1 inch to about 4½ inches, in other embodiments, the distal end portion of the bag 20" can have a depth between about 2½ inches and about 4 inches, and in other embodiments, the distal end portion of the bag can have a depth between about 3¼ inches and about 3¾ inches.

In terms of a ratio of depth of the distal end portion 160 of the bag 20" to the total depth of the bag 20" between the open end and the closed end, in some embodiments, the ratio of the depth of the lower portion of the bag 20" to the total depth is between about 1:3 and about 1:1.1, in other embodiments, the ratio of the depth of the distal-end portion of the tissue retrieval bag to the total depth of the beg is between about 1:2.2 and about 1:1.3, and in other embodiments, the ratio of the depth of the distal-end portion of the retrieval bag to the total depth of the tissue retrieval bag is between about 1:2 and about 1:1.5.

In the illustrated embodiment, the second film material comprises a 0.004" or 4 mil polyurethane film material, although in different embodiments, different thicknesses of film can be used, such as, for example, 2 mil film, 6 mil film, or film of another suitable thickness. Furthermore, in other embodiments, the second film material can comprise another suitable film material.

As illustrated, the second film material comprising the distal end portion 160 of the retrieval bag 20" has a modulus of about 1600 PSI at 100% elongation. In other embodiments, the modulus can be different, although always relatively high when compared to the modulus of first film material for the cuff portion 158 in the corresponding embodiment. For example, in other embodiments, the modulus of the second film material can be between about 1000 PSI at 100% elongation and about 2200 PSI at 100% elongation. In still other embodiments, the modulus can be between about 1200 PSI at 100% elongation and about 2000 PSI at 100% elongation. In other embodiments, the modulus can be between about 1500 PSI at 100% elongation and about 1700 PSI at 100% elongation.

The relatively low modulus material in the cuff portion 158 of the retrieval bag 20" can allow the bag 20" to be easily opened and closed while the relatively high modulus material in the lower distal-end portion 160 of the retrieval bag 20" can reduce or substantially prevent elongation of the retrieval bag and force the specimen itself to take on the shape of the retrieval bag. Thus, the described hybrid retrieval bag 20" can provide eased withdrawal of the retrieval bag from the body cavity as compared to a comparable non-hybrid bag.

With reference to FIG. 12, other embodiments of hybrid retrieval bag 20" are illustrated including at least two portions having film material of different thicknesses. A retrieval bag 20" formed with two different thicknesses of film material can be advantageous in that the cuff portion 158' of the retrieval bag 20" can be formed of a smaller gauge film than in a distal-end portion 160' of the retrieval bag 20". Thus, the cuff portion 158' of the retrieval bag is relatively compliant compared to the distal-end portion 160'.

The strength and puncture resistance of the distal-end portion 160' of the retrieval bag 20" can be enhanced by utilizing a relatively larger gauge film. A larger gauge film can be used in the distal-end portion 160' of the retrieval bag than would otherwise be possible if the retrieval bag with the same shape and size were to be manufactured entirely from a uniform thickness film. By incorporating a relatively thin film in the cuff portion 158' of the retrieval bag and a relatively thick film in the distal-end portion 160' of the retrieval bag 20", the volume of the bag when rolled and stored in the introducer tube 3 can be substantially equivalent to the volume of retrieval bag formed with a uniform film thickness. But, the hybrid retrieval bag 20" can have a significantly greater strength in the distal-end portion 160' of the retrieval bag (where strength can be highly desirable) than a comparable non-hybrid uniform film thickness bag.

In the illustrated embodiment, the distal-end portion 160' of the retrieval bag 20" has a circumference which is significantly less than a circumference of the cuff portion 150' of the retrieval bag. As discussed above, for a retrieval bag formed from a uniform thickness film, the stress transferred to the cuff portion of the retrieval bag during withdrawal of the bag from a patient by cinching the cord loop 132 through the cuff 130 is significantly less than the stress transferred to the lower distal portion of the tissue bag. Thus, a thin gauge film can be used in the cuff portion 158' of the retrieval bag to provide a desired tensile strength while a thick gauge film can be used in the distal-end portion 160' of the retrieval bag 20" to provide increased tensile strength, increased hoop strength, and increased puncture resistance. In various embodiments, these improvements can be obtained in hybrid tissue retrieval bags 20" using two thicknesses of the same film material or two thicknesses of different film materials.

With continued reference to FIG. 12, one exemplary embodiment of a hybrid retrieval bag 20" can have a cuff portion 158' with an internal diameter of about 2.75" and a wall thickness of about 2 mil in the cuff portion. Accordingly, the cuff portion 158' of the illustrated embodiment of retrieval bag 20" will experience a tensile stress of about 1735 PSI under a tensile load of about 30 pounds.

In the illustrated embodiment, the same retrieval bag 20" can have an internal diameter of about 0.75" and a wall thickness of about 6 mil at the distal end of the bag. Accordingly, the distal end portion of the illustrated embodiment of retrieval bag will experience a tensile stress of about 2105 PSI under a tensile load of about 30 pounds. Thus, advantageously, the tensile stresses encountered by the illustrated tissue retrieval bag 20" are substantially more balanced as compared with the exemplary comparable uniform, non-hybrid tissue retrieval bag described above.

With continued reference to FIG. 12, while the illustrated embodiment of retrieval bag 20" includes a cuff portion 158' having a 2 mil film thickness and a distal end portion 160' having a 6 mil film thickness, it is contemplated that in other embodiments, other film thicknesses can be used. For example, in some embodiments, the cuff portion can have a film thickness of between about 1 mil and about 5 mil, in other embodiments, the cuff portion can have a film thickness of between about 2 mil and about 4 mil. In some embodiments, the distal portion can have a film thickness greater than that of the cuff portion of the corresponding embodiment and between about 3 mil and about 9 mil, in other embodiments, the distal portion can have a film thickness greater than that of the cuff portion of the corresponding embodiment and between about 5 mil and 7 mil.

Advantageously, a hybrid retrieval bag 20" with varying wall thicknesses, can have substantially balanced stresses between the cuff portion 158' and the distal-end portion 160'. Thus, a hybrid retrieval bag can be configured to provide a desired strength at the distal end while maintaining compliance at the cuff for installation in an inserter tube. In some embodiments, the material thicknesses of the cuff portion and distal portion of the hybrid retrieval bag can be chosen such that for a predetermined tensile load, the corresponding tensile stresses are equal.

Figure 13:
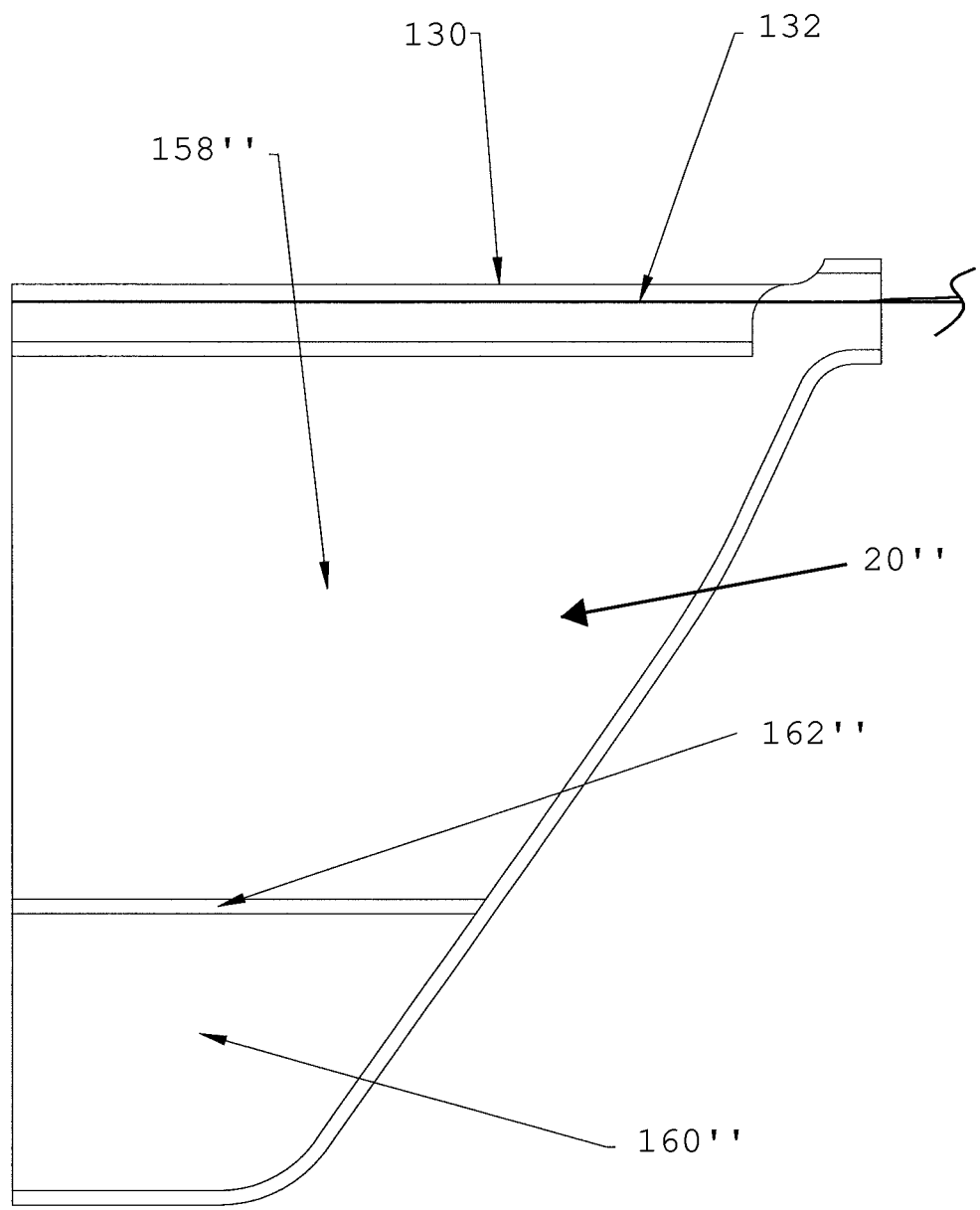
FIG. 13 is a side view of one embodiment of hybrid tissue retrieval bag.

With reference to FIG. 13, in some embodiments of hybrid tissue retrieval bag 20", the retrieval bag 20" can be formed with a reinforced wall segment in the distal-end portion 160" of the bag. As discussed above, during withdrawal of the retrieval bag 20" through a body wall, the specimen is typically forced into the distal-end portion 160" of the bag, subjecting this portion of the retrieval bag to high stresses. The distal portion of the retrieval bag typically has the least cross-sectional area for supporting a tensile load and it is therefore advantageous to enhance the strength of the distal portion of the retrieval bag. Thus, in some embodiments, it can be advantageous to increase the strength of the distal-end portion 160" of the retrieval bag by providing a reinforced section, such as a multiple layer wall section. In the illustrated embodiment, the reinforced section comprises a double wall configuration in the distal-end portion 160" of the retrieval bag 20". Advantageously, by providing a reinforced section in only the distal-end portion 160" of the retrieval bag 20", the tensile strength of the distal-end portion 160" of the bag 20" can be relatively increased while maintaining the rolled volume of the retrieval bag 20" at a relatively small diameter compared to a non-hybrid retrieval bag having equivalent tensile strength at the distal end. Thus, the hybrid retrieval bag 20" can be rolled and stored in a relatively low-diameter introducer tube 3 as compared to a non-hybrid retrieval bag having equivalent tensile strength at the distal end.

In some embodiments, the reinforced section of the hybrid retrieval bag 20" comprises at least two layers of the same film material. In other embodiments, the reinforced section comprises at least two layers of different film materials. Moreover, in some embodiments, the reinforced section is formed with at least two layers of the same film material each having different thicknesses. In other embodiments, the reinforced section is formed of at least two layers of different film materials each having different thicknesses. In still other embodiments, the reinforced section is formed of at least two layers of film material having a substantially identical thickness.

In some embodiments, the hybrid retrieval bag 20" with a reinforced section can be reinforced with a very stiff high modulus, high-strength material that might not otherwise be suitable on its own for manufacturing a retrieval bag. For example in one embodiment, a retrieval bag formed of a polyurethane film can be reinforced with a fabric material such as a non-coated rip stop nylon to prevent the distal portion of the retrieval bag from deforming during withdrawal from a body cavity.

In certain embodiments, the reinforced section of the distal-end portion 160" can be coupled to the hybrid retrieval bag 20" in various ways. For example, in various embodiments, the reinforced section can be chemically adhered to the retrieval bag with a bio-compatible chemical adhesive. In other embodiments, the reinforced section can be thermally fused to the tissue retrieval bag. In other embodiments, the reinforced section can be ultrasonically welded to the retrieval bag. In some embodiments, the reinforced section can be overmolded or dip molded onto the retrieval bag. In some embodiments, the reinforced section can be sewn onto the retrieval bag. The hybrid specimen retrieval bags 20" illustrated in FIGS. 11-12 can be formed with similar processes for joining the cuff portions 158, 158' to the distal-end portions 160, 160', as discussed with respect to the specimen retrieval bags 20" of FIG. 13, and can each include a joint 162, 162' between the corresponding cuff portions 158, 158' and distal-end portions 160, 160'.

With continued reference to FIG. 13, in some embodiments a hybrid retrieval bag 20" with a reinforced section can have an external joint 162" such as a weld or seam extending along an outer surface of the tissue retrieval bag between the reinforced section of the distal-end portion 160" and the cuff portion 158" of the tissue retrieval bag 20". In other embodiments, the reinforced section of the distal-end portion 160" can be disposed on an interior surface of the retrieval bag 20" such that an internal joint such as a weld or seam extends along the inner surface of the tissue retrieval bag.

In some embodiments, the reinforced section is coupled to the distal portion of the retrieval bag 20" over substantially an entire inner surface of the reinforced section. For example, in some embodiments, the reinforced section 20" can comprise a laminate of two layers of film material. In other embodiments, the reinforced section is coupled to the distal-end portion 160" of the retrieval bag 20" over a portion of the inner surface of the reinforced section such that one or more gaps or cavities is formed between the reinforced section and the retrieval bag. For example, in some embodiments, the reinforced section can be coupled to the retrieval bag 20" at a substantially curvilinear joint, seam, or weld at a proximal end of the reinforced section while a cavity is formed between the retrieval bag and substantially all of the reinforced section distal of the joint, seam, or weld. In other embodiments, a portion of the joint, seal, or weld can extend distally from the proximal end of the reinforced section towards the distal, closed end of the retrieval bag such that more than one gap or cavity is created between the reinforced section and the retrieval bag 20".

In embodiments of tissue retrieval bag 20" having at least one gap or cavity between the reinforced section and the retrieval bag, the tissue retrieval system can include a vent fluidly coupling the at least one gap or cavity to ambient conditions exterior to the tissue retrieval system or to the interior of the tissue retrieval bag. Thus, in vented embodiments of tissue retrieval system, a volume of gas in the gap or cavity of the tissue retrieval system would not restrict the assembly, foldability or rollability of the tissue retrieval system due to consequent compression of the volume of gas within the gap or cavity. In some embodiments, the vent can comprise one or more unjoined segments along the joint such as intermittent weld or small breaks in the weld of a welded seam (as illustrated, for example, in the gap 64 in seam 62 of the retrieval bag 20' illustrated in FIG. 7). In other embodiments, the joint can be substantially contiguous, and the vent can comprise one or more holes in the reinforced section fluidly coupling the gap or cavity to ambient conditions, or one or more holes in the tissue retrieval bag under the reinforced section.

As discussed above, a comparable non-hybrid retrieval bag with an internal distal diameter of about 0.75" and a wall thickness of about 4 mil at the distal end of the bag will experience a tensile stress of about 3166 PSI under a tensile load of about 30 pounds. With continued reference to FIG. 13, an exemplary embodiment of hybrid retrieval bag comprises a 4 mil material with a reinforced section of an additional 4 mil film layer at the distal portion. In the illustrated embodiment, the tissue retrieval bag can have an internal diameter of about 0.75" and a wall thickness of about 8 mil (comprised of two 4 mil layers), at the distal end portion 160" of the bag. The illustrated hybrid specimen retrieval bag 20" will experience a tensile stress of about 1575 PSI at the distal-end portion 160" under a tensile load of about 30 pounds. Thus, advantageously, by providing a retrieval bag with a reinforced section having a double-layer wall at the distal-end portion 160" of the retrieval bag 20", the overall strength of the retrieval bag 20" can be significantly increased.

With reference to FIGS. 14-15, in some embodiments of hybrid tissue retrieval bag, the tissue retrieval bag 20" can have a compliant cuff 130', 130" through which a cord loop 132 passes and a bag portion 180 extending from the cuff 130', 130" to the closed end of the bag 20". The cuff 130', 130" can be relatively compliant relative to the bag portion 180. In some embodiments, the bag portion 180 can comprise an upper bag portion and a lower bag portion, each having different properties (for example, the bag portion 180 can be similar to the upper cuff portion and lower distal end portion of one of the hybrid retrieval bags described with respect to FIGS. 11-13 with the compliant cuff 130', 130" desirably being more compliant than an upper cuff portion of the hybrid retrieval bag 20" described with respect to FIGS. 11-13).

In some embodiments, the cuff 130', 130" can include various compliance enhancing features. Increasing the compliance of the cuff 130', 130" facilitates the opening and closure of the retrieval bag 20" and enables retrieval bag 20" to be formed from a film material with a greater thickness than would otherwise be possible in a comparable non-hybrid retrieval bag. Increasing the compliance of the cuff also enables retrieval bag to be formed from a material with a higher modulus than would otherwise be possible. Increasing the retrieval bag material modulus and/or thickness improves the tensile strength of the retrieval bag.

In various embodiments, the cuff 130', 130" can include one or more of various compliance enhancing features such as holes 130' (FIG. 14), slots 130" (FIG. 15), slits, or notches in the cuff to provide the cuff with increased compliance. In some embodiments, the compliance enhancing features can be die cut into an otherwise solid cuff during manufacture of the retrieval bag. In other embodiments, other manufacturing techniques can be used to form the compliance enhancing features.

In one method of manufacture, the cuff of the retrieval bag 20" can be formed by folding the film at the open end of the retrieval bag over on itself and joining the film to itself such as by an adhesive bonding, thermal welding, or ultrasonic welding process. This folded and joined segment of film forms a cuff channel bounded by two film walls. A closure member and retrieval bag supports can pass through the cuff channel. As described above, in use, after the retrieval bag supports are withdrawn from the cuff channel, the cord loop is then tensioned and the cuff channel is forced to fold longitudinally thereby cinching the bag closed. In various embodiments, the holes, slots, slits, or notches can be formed through one or both of the walls of the cuff channel to provide a desired degree of compliance.

It is contemplated that various configurations and arrangements of compliance enhancing features can be included in various embodiments of hybrid retrieval bag 20" having a compliant cuff. In some embodiments, the compliance enhancing features are provided circumferentially throughout the peripheral extent of the cuff. In other embodiments compliance enhancing features are provided circumferentially over a portion of the peripheral extent of the cuff. For example, in the embodiments illustrated in FIGS. 14 and 15, a distal tip region of the cuff has no compliance enhancing features. In some embodiments, compliance enhancing features are provided throughout a depth of the cuff of the retrieval bag. In other embodiments, compliance enhancing features are provided over a portion of the depth of the cuff of the retrieval bag. In some embodiments, compliance enhancing features are of uniform size throughout the cuff portion. In other embodiments, compliance enhancing features vary in size along the cuff. For example, in some embodiments, at least some of the compliance enhancing features can be sized to prevent to prevent the retrieval bag supports from protruding through the wall of the cuff during deployment of the retrieval bag from the introducer tube.

In various embodiments of any of the above-described embodiments of hybrid specimen retrieval bag, various aspects of the device can vary. For example, in certain embodiments, the retrieval bag can be formed of one or more of a variety of materials, including polyurethane, polyethylene, polyimide, rip stop Nylon®, polyester, and Mylar®.

While as discussed above with respect to FIG. 13, the hybrid retrieval bag 20" can include a reinforced section at the distal-end portion 160" of the bag 20", in other embodiments, any of the retrieval bags described herein the retrieval bag can be reinforced along the axis of the cord loop length and/or transverse to the axis of the cord loop to minimize the elongation of the bag during withdrawal from the body cavity. For example, in various embodiments, a mesh material, strips of a film material, strips of a woven fabric, cord, or wire can be attached to the retrieval bag to reinforce the bag and prevent elongation and deformation of the bag.

While as discussed above with respect to FIG. 11, the retrieval bag 20" can be formed of two portions 158, 160 of material having different properties, in some embodiments, the retrieval bag can be formed of more than two portions of material each having different properties. For example, FIG. 11 illustrates a bag having a first material for the cuff portion with a relatively high compliance and a second material for the distal portion having a relatively low compliance. In another embodiment, the retrieval bag can be formed from three or more different film materials such that the cuff portion is formed of a low modulus, highly flexible material, an intermediate portion is formed of a media modulus, moderately flexible material, and the distal portion could be formed of a high modulus, relatively inflexible material.

Additionally, while FIG. 12 illustrates a tissue retrieval bag having two portions of material having different thicknesses, in some embodiments, a retrieval bag is formed from three or more portions of material each having different thicknesses. For example, in some embodiments, the cuff portion is formed of a thin material, such as a 2 mil thick film, the intermediate portion is formed of a moderately thick material such as a 6 mil thick film, and the distal portion is formed of a relatively thick material such as an 8 mil thick film.

Moreover, while FIG. 13 illustrates a retrieval bag having a reinforced section with an additional layer of film material at the distal end, in another embodiment, a retrieval bag can have an intermediate portion having an intermediate level of reinforcement such as two layers of film material and relatively highly reinforced section at a distal end portion such as with three or more layers of film material.

In some embodiments, a hybrid retrieval bag can be formed of a single film material which progressively increases in wall thickness from the proximal open end of the retrieval bag to the distal closed-end of the retrieval bag. In these embodiments, the retrieval bag can advantageously have a relatively high strength at the closed end and a relatively high compliance at the open end.

As discussed above a tissue retrieval system having a hybrid tissue retrieval bag can be manufactured in a range of sizes and configurations to accommodate varying clinical needs. In certain embodiments, the tissue retrieval systems can include a 5 mm diameter introducer tube to enable introduction through a 5 mm trocar. In other embodiments, a tissue retrieval system can include a 10 mm introducer tube to enable introduction through a 10 mm trocar. In other embodiments, a tissue retrieval system can include a 15 mm introducer to provide a larger retrieval bag for introduction through a 15 mm trocar.

In some embodiments, a hybrid tissue retrieval bag can be provided as a standalone device without introducer tube, handle, or delivery device. The hybrid retrieval bag, in this aspect, would be provided with a closure member such as a cord loop. In use, the standalone tissue retrieval bag is rolled or folded by a surgeon and then advanced through a trocar into a body cavity with the use of a laparoscopic grasper. In some embodiments, the standalone retrieval bag can be provided with a guide bead to enable the retrieval bag to be cinched closed and reopened within the body cavity as necessary. In other embodiments, the standalone retrieval bag could be provided with a slipknot in the cord loop to enable the retrieval bag to be cinched closed within the body cavity.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. For example, while various lengths and ratios of depths are discussed with respect to the hybrid specimen retrieval bag of FIG. 11, it is contemplated that these descriptions are equally applicable to the hybrid retrieval bags of FIGS. 7-8 and 12-13. Thus, it is intended that the scope of the present inventions herein disclosed should not be limited by the particular disclosed embodiments described above, but should be determined only by a fair reading of the claims pursued in a non-provisional application claiming priority hereto.

What is claimed is:

1. A tissue retrieval device comprising:
a tissue bag having an open end, a closed end, and an interior, the tissue bag comprising:
a first portion adjacent the open end; and
a second portion adjacent the closed end, the second portion comprising:
a first layer;
a second layer;
a space between the first and second layer; and
at least one vent fluidly coupling the space to ambient conditions exterior to the tissue bag;
wherein the second portion comprises a joint coupling the first layer and the second layer; and
wherein the vent comprises a gap in the joint.

2. The tissue retrieval device of claim 1, wherein the retrieval bag has a total depth extending between the open end and the closed end, wherein the first portion has a first depth extending from the open end to the joint, and wherein a ratio of the first depth to the total depth is between about 1:2 and 1:3.

3. The tissue retrieval device of claim 1, wherein the first portion of the retrieval bag comprises a first material, and the second portion of the retrieval bag comprises a second material different from the first material.

4. The tissue retrieval device of claim 1, wherein the first portion of the retrieval bag has a first thickness, and the second portion of the retrieval bag has a second thickness different from the first thickness.

5. The tissue retrieval device of claim 4, wherein the second thickness is greater than the first thickness.

6. The tissue retrieval device of claim 5, wherein the first portion comprises a first thickness of approximately 4 mil, and the second portion comprises a thickness of approximately 8 mil.

7. The tissue retrieval device of claim 1, wherein the first portion comprises a first material having a first modulus of elasticity and the second portion comprises a second material having a second modulus of elasticity greater than the first modulus of elasticity.

8. The tissue retrieval device of claim 1, wherein the joint comprises at least one of a welded connection, a bonded connection, and a sewn connection.

9. The tissue retrieval device of claim 1, wherein the retrieval bag comprises at least one of a polyurethane film, a polyethylene film, a polyimide film, ripstop Nylon®, polyester, and Mylar®.

10. The tissue retrieval device of claim 1, wherein the first portion of the retrieval bag comprises a cuff adapted to receive at least one support member therein.

11. The tissue retrieval device of claim 1, further comprising a cord positioned in the first portion and operable to selectively close the open end of the bag.

12. The tissue retrieval device of claim 11, wherein the first portion comprises a cuff having a passage therein and the cord is positioned in the passage.

* * * * *